(12) United States Patent
Ben-Haim et al.

(10) Patent No.: US 11,806,126 B2
(45) Date of Patent: Nov. 7, 2023

(54) PROPERTY- AND POSITION-BASED CATHETER PROBE TARGET IDENTIFICATION

(71) Applicant: Navix International Limited, Road Town (VG)

(72) Inventors: Shlomo Ben-Haim, Milan (IT); Yitzhack Schwartz, Haifa (IL); Zalman Ibragimov, Rehovot (IL)

(73) Assignee: Navix International Limited, Road Town (VG)

( * ) Notice: Subject to any disclaimer, the term of this patent is extended or adjusted under 35 U.S.C. 154(b) by 811 days.

(21) Appl. No.: 16/612,385

(22) PCT Filed: May 10, 2018

(86) PCT No.: PCT/IB2018/053258
§ 371 (c)(1),
(2) Date: Nov. 10, 2019

(87) PCT Pub. No.: WO2018/207128
PCT Pub. Date: Nov. 15, 2018

(65) Prior Publication Data
US 2020/0196908 A1    Jun. 25, 2020

Related U.S. Application Data

(60) Provisional application No. 62/504,339, filed on May 10, 2017.

(51) Int. Cl.
*A61B 5/06* (2006.01)
*A61B 34/20* (2016.01)
(Continued)

(52) U.S. Cl.
CPC ............ *A61B 5/063* (2013.01); *A61B 5/0538* (2013.01); *A61B 5/6853* (2013.01); *A61B 18/02* (2013.01);
(Continued)

(58) Field of Classification Search
CPC ..... A61B 5/063; A61B 5/0538; A61B 5/6853; A61B 18/02; A61B 18/1477; A61B 34/20;
(Continued)

(56) References Cited

U.S. PATENT DOCUMENTS

| 5,391,199 A | * | 2/1995 | Ben-Haim | ............... A61N 1/06 |
| | | | | 607/122 |
| 6,983,179 B2 | * | 1/2006 | Ben-Haim | ........... A61B 5/6852 |
| | | | | 600/374 |

(Continued)

FOREIGN PATENT DOCUMENTS

| EP | 1472975 | 11/2004 |
| EP | 1853162 | 11/2007 |

(Continued)

OTHER PUBLICATIONS

International Preliminary Report on Patentability dated Nov. 21, 2019 From the International Bureau of WIPO Re. Application No. PCT/IB2018/053258. (8 Pages).

(Continued)

*Primary Examiner* — Oommen Jacob

(57) ABSTRACT

Methods and systems for position determination of an intrabody probe, targets of an intrabody probe, and or actions to be performed using an intrabody probe are described. In some embodiments, an anatomy being navigated and/or mapped is described by a rule-based schema relating different anatomically identified structures to one another according to their ability to help identify and/or (Continued)

locate one another. Additionally, in some embodiments, data recorded from the intrabody probe is processed according to schema rules in order to provide anatomical identification of the anatomical region which the intrabody probe is sampling, optionally without performing detailed mapping, and/or prior to the availability of detailed mapping of anatomical geometry.

17 Claims, 17 Drawing Sheets

(51) Int. Cl.
*A61B 34/00* (2016.01)
*G06N 20/00* (2019.01)
*A61B 5/0538* (2021.01)
*A61B 5/00* (2006.01)
*A61B 18/02* (2006.01)
*A61B 18/14* (2006.01)
*A61B 18/00* (2006.01)

(52) U.S. Cl.
CPC .......... *A61B 18/1477* (2013.01); *A61B 34/20* (2016.02); *A61B 34/25* (2016.02); *G06N 20/00* (2019.01); *A61B 2018/0022* (2013.01); *A61B 2018/00357* (2013.01); *A61B 2018/00375* (2013.01); *A61B 2018/00577* (2013.01); *A61B 2018/0212* (2013.01); *A61B 2034/2046* (2016.02)

(58) Field of Classification Search
CPC ............ A61B 34/25; A61B 2018/0022; A61B 2018/00357; A61B 2018/00375; A61B 2018/00577; A61B 2018/0212; A61B 2034/2046; A61B 18/1492; A61B 2017/00026; A61B 2018/1475; A61B 2034/2051; A61B 2034/2053; A61B 5/1076; A61B 17/1204; A61B 17/12109; A61B 17/12136; G06N 20/00
See application file for complete search history.

(56) References Cited

U.S. PATENT DOCUMENTS

| | | | |
|---|---|---|---|
| 9,332,928 B2 † | 5/2016 | Markowitz | |
| 2007/0073151 A1* | 3/2007 | Lee | A61B 17/2202 600/439 |
| 2009/0264745 A1* | 10/2009 | Markowitz | A61B 5/053 600/509 |
| 2010/0135561 A1* | 6/2010 | Moulik | G06T 7/0012 382/131 |
| 2012/0035452 A1* | 2/2012 | Jalde | A61B 5/42 600/380 |
| 2012/0089028 A1* | 4/2012 | Hadani | A61B 8/12 600/459 |
| 2014/0107510 A1* | 4/2014 | Bogun | A61B 5/316 600/523 |
| 2015/0164605 A1* | 6/2015 | Patwardhan | A61B 8/5207 600/417 |
| 2015/0182726 A1* | 7/2015 | Jenkins | A61M 25/0113 600/424 |
| 2016/0120522 A1* | 5/2016 | Weingarten | A61B 6/487 378/42 |
| 2018/0160981 A1* | 6/2018 | Tsymbalenko | A61B 8/5215 |
| 2020/0196908 A1* | 6/2020 | Ben-Haim | A61B 5/1076 |

FOREIGN PATENT DOCUMENTS

| | | |
|---|---|---|
| WO | WO 2016/088084 | 6/2016 |
| WO | WO 2018/207128 | 11/2018 |

OTHER PUBLICATIONS

International Search Report and the Written Opinion dated Aug. 13, 2018 From the International Searching Authority Re. Application No. PCT/IB2018/053258. (15 Pages).

\* cited by examiner
† cited by third party

PROPERTY- AND POSITION-BASED CATHETER PROBE TARGET IDENTIFICATION

RELATED APPLICATIONS

This application is a National Phase of PCT Patent Application No. PCT/IB2018/053258 having International filing date of May 10, 2018, which claims the benefit of priority under 35 USC § 119(e) of U.S. Provisional Patent Application No. 62/504,339 filed on May 10, 2017.

PCT Patent Application No. PCT/IB2018/053258 is also related to U.S. Provisional Patent Application No. 62/362,146 filed on Jul. 14, 2016 and entitled "CHARACTERISTIC TRACK CATHETER NAVIGATION"; U.S. Provisional Patent Application No. 62/422,748 filed on Nov. 16, 2016 and entitled "ESTIMATORS FOR ABLATION EFFECTIVENESS"; and U.S. Provisional Patent Application No. 62/422,767 filed on Nov. 16, 2016 and entitled "ESOPHAGUS POSITION DETECTION BY ELECTRICAL MAPPING".

The contents of the above applications are all incorporated by reference as if fully set forth herein in their entirety.

FIELD AND BACKGROUND OF THE INVENTION

The present invention, in some embodiments thereof, relates to the field of navigation of body cavities by intrabody probes, and more particularly, to determination of intra-body probe position, for example during navigation of body cavities.

Several medical procedures in cardiology and other medical fields comprise the use of intrabody probes such as catheter probes to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electrical field-guided position sensing systems.

SUMMARY OF THE INVENTION

There is provided, in accordance with some embodiments of the present disclosure, a method of determining an anatomical identity of a first intrabody region using an intrabody probe, the method comprising: receiving data indicating an operational context; receiving input data from the intrabody probe indicating one or more measured properties of the first intrabody region; selecting at least one rule for anatomical identification from an anatomical schema, wherein the at least one rule is selected based on the operational context; and applying the at least one rule to the input data, to determine anatomical identity of the first intrabody region.

In some embodiments, the method comprises: selecting a second at least one rule for anatomical identification from the anatomical schema, based on the current operational context; and applying the second at least one rule to identify a second intrabody region, based on a relationship between the second intrabody region and the first intrabody region expressed by a rule of the anatomical schema, and the anatomical identity determined for the first intrabody region.

In some embodiments, the method comprises associating the anatomical identity determined for the first region to a geometrical representation of the first intrabody region.

In some embodiments, the method comprises displaying the anatomical identity determined for the first intrabody region together with a display of the geometrical representation of the first intrabody region.

In some embodiments, the method comprises guiding navigation of the intrabody probe to the first intrabody region, based on the anatomical identity determined for the first intrabody region.

In some embodiments, the method comprises using the intrabody probe to perform an action upon the first intrabody region, based on the anatomical identity determined for the first intrabody region.

In some embodiments, the input data does not include image data.

In some embodiments, the data indicating a current operational context comprise non-image data.

In some embodiments, the input data comprises electrical measurements from the intrabody region.

In some embodiments, the electrical measurements comprise voltage measurements.

In some embodiments, the electrical measurements comprise impedance measurements.

There is provided, in accordance with some embodiments of the present disclosure, a method of generating an estimator of an anatomical identity of an intrabody region based on input data collected from an intrabody probe, comprising: obtaining a plurality of indications from at least one skilled operator of the intrabody probe, wherein the indications are of an anatomical identity of intrabody regions corresponding to different intrabody positions of the intrabody probe while the input data was collected; and processing the input data together with the plurality of indications to generate an estimator configured to identify the intrabody region, based on new input data collected from an intrabody probe.

In some embodiments, the input data comprises electrical measurements from the intrabody region.

In some embodiments, the processing comprises processing to generate a plurality of the estimators, each for identifying a corresponding intrabody region, based on the input data and the plurality of indications.

In some embodiments, the processing comprises application of a machine learning method.

There is provided, in accordance with some embodiments of the present disclosure, a method of crossing an interatrial septum, comprising: recording the position of an intrabody probe at multiple locations adjoining the interatrial septum while the intrabody probe measures data indicating a tissue property of the interatrial septum at each of the multiple locations; and identifying the thinnest zone of the interatrial septum, based on electrical measurements in the right atrium; and providing the crossing location across which the intrabody probe is to be moved, based on the identification of the thinnest zone.

In some embodiments, the measured indicating data comprise an electrical field parameter affected by the indicated tissue property.

In some embodiments, the intrabody probe comprises a needle, and the data indicating the tissue property is electrically sensed using the needle.

In some embodiments, the method comprises sensing a change in an electrical signal as the needle extends from a sheath to cross the crossing location, and displaying tenting movement of a simulated display of the interatrial septum in correspondence with the sensed change in the electrical signal.

In some embodiments, the moving the intrabody probe across the crossing location comprises ablating at the crossing location using the probe to weaken tissue at the crossing location.

In some embodiments, the method comprises using the same intrabody probe to perform another ablation in a heart chamber entered after crossing the crossing location.

There is provided, in accordance with some embodiments of the present disclosure, a method of verifying the placement of a cryoballoon, comprising: monitoring output from a sensing electrode of an intrabody probe as the electrode is inserted into an opening of a pulmonary vein; detecting a predetermined change in the output of the sensing electrode; and providing an indication of occlusion of the opening, based on the detection of the predetermined change.

In some embodiments, the occlusion of the opening is sufficient to block blood flow through the opening.

In some embodiments, the indication comprises an indication that the intrabody probe is in a position suitable for ablation.

In some embodiments, the suitable position comprises the cryoballoon being in contact with tissue near the vein opening around an uninterrupted perimeter.

There is provided, in accordance with some embodiments of the present disclosure, an apparatus for determining an anatomical identity of an intrabody region, the apparatus comprising: an interface configured to receive from a user of the apparatus data indicating an operational context; an intrabody probe input for receiving input data from the intrabody probe indicating one or more measured properties of the intrabody region; a memory storing a plurality of rules for determining the identity of the intrabody region, each rule being associated with a respective operational context; and a processor configured to: select at least one rule from the memory based on the operational context received through the interface; and determine the anatomical identity of the intrabody region by applying the at least one rule to the input data.

In some embodiments, the processor is configured to associate the determined anatomical identity to a geometrical representation of the intrabody region.

In some embodiments, the processor is also configured to provide for display the anatomical identity together with the geometrical representation of the intrabody region.

There is provided, in accordance with some embodiments of the present disclosure, a method of determining an action to perform within an intrabody region using an intrabody probe, the method comprising: receiving data indicating an operational context, as well as a target selection indicating an anatomical portion of the intrabody region upon which an action is to be performed; receiving input data from the intrabody probe indicating one or more measured properties of the intrabody region; selecting at least one rule for determining the action from a procedure schema, wherein the at least one rule is selected based on the current operational context and the target selection; and applying the at least one rule to the input data, to determine the action.

In some embodiments, the determined action comprises guiding navigation of the intrabody probe to the anatomical portion indicated by the target selection.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon.

Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
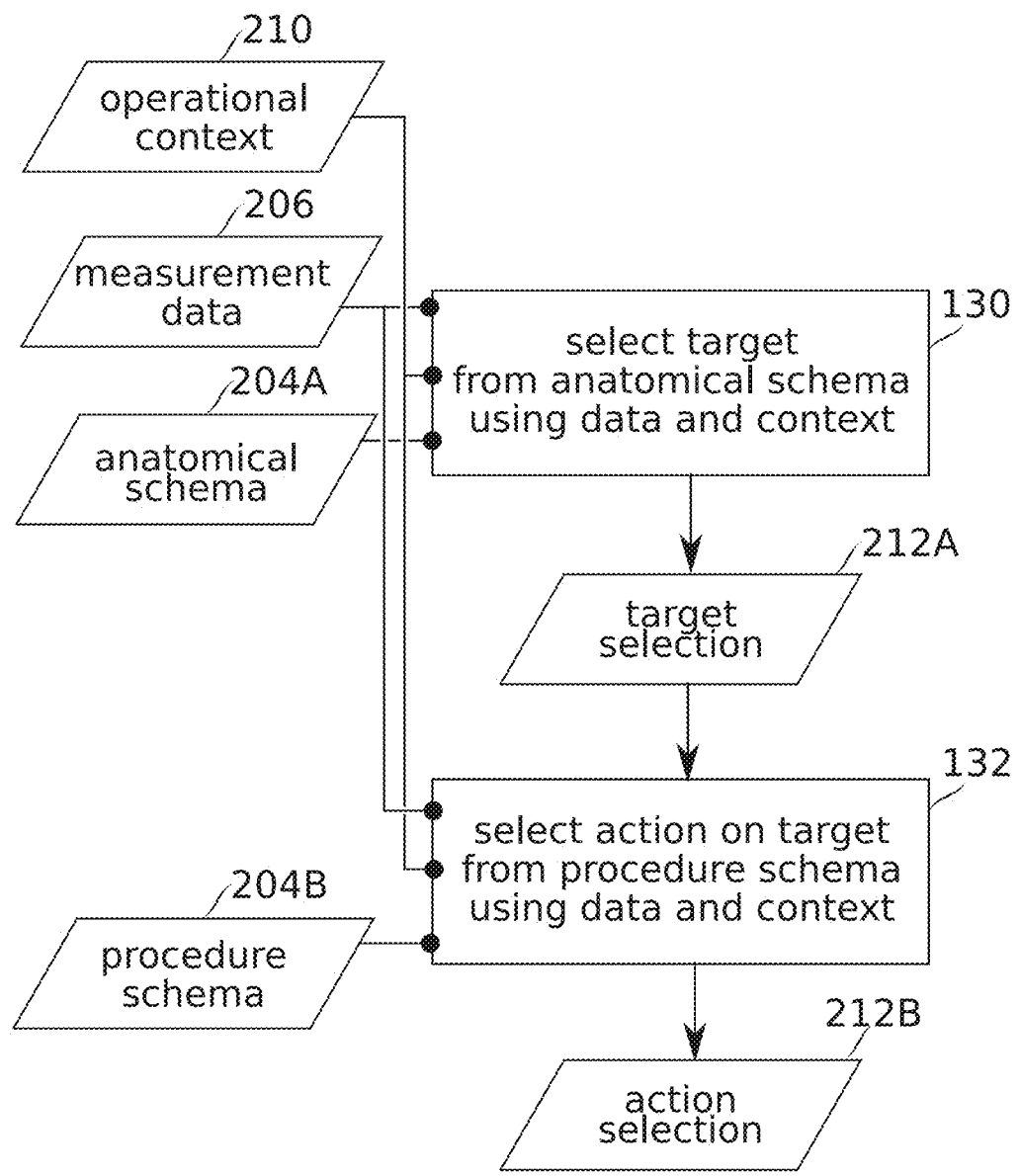
FIG. 1A schematically represents a method of automatic anatomical identification of an intrabody target, and optionally automatic suggestion of a selected action on that target, according to some embodiments of the present disclosure.

The present invention, in some embodiments thereof, relates to the field of navigation of body cavities by intra-body probes, and more particularly, to determination of intra-body probe position, for example during navigation of body cavities.

Overview

A broad aspect of some embodiments of the present invention relates to use of catheter probe measurements to establish anatomical identity of intrabody regions, particularly intrabody regions in the vicinity of the probe.

Methods for determining the anatomical geometry of intrabody regions navigated by catheters have been described based on many different techniques; for example, CT imaging, X-ray angiographic imaging, MRI imaging, ultrasound imaging, electrical field-guided probe navigation, and magnetic field-guided probe navigation.

Some such methods build up a reconstruction of anatomical geometry based at least in part on data acquired on the fly during a catheterization procedure. For example, methods using electrical field-guided probe navigation may use electrically recorded data to build up an anatomical model which gradually increases in coverage, resolution, and/or accuracy as a procedure progresses. Accordingly, an operator may be presented with a need to perform procedure operations based on incomplete geometrical information. Moreover, and potentially even in situations where anatomical geometry is well-represented, an operator (particularly an inexperienced operator) may occasionally become confused in making an anatomical identification based on anatomical geometry information alone.

Misidentification of anatomical position, even if rare, potentially leads to serious complications. For example, trans-septal passage of an intracardiac catheter is a complicated intervention, which even after 200 cases of training has been associated with a risk of serious adverse events in the range of about 2%. One type of adverse event comprises penetration of the wrong part of the heart wall. Potentially, improvements in making the link between anatomical geometry and identification of that geometry as being of a particular (e.g., named) anatomical structure would help reduce such rates of complication.

Herein, a distinction is drawn between anatomical geometry and anatomical identity. Anatomical geometry comprises shapes of anatomy, and relationships among those shapes in the definition of larger structures. As examples of anatomical geometry: a heart chamber has a (dynamically changing) roughly globular shape, from which one or more tubular blood vessels extend; the heart chamber also is in fluid communication with another roughly globular-shaped heart chamber. Anatomical identity comprises assigning to an anatomical position an identity as belonging to a particular anatomically defined structure, such as a right atrium, pulmonary vein, or even more particularly, for example, as an interatrial septum, foramen ovale, ostium of a pulmonary vein, atrial appendage, and/or another anatomical structure. The identified position may be a position defined within a modeled anatomical geometry; for example, the position of a shape appearing in the model or any portion thereof. In some embodiments, the identified position may be a point-like position.

Anatomical identity of a position can generally be deduced from a sufficiently complete representation of anatomical geometry (e.g., by consideration of shapes at the position itself and/or the relationship of the position to shapes in other, e.g., adjacent, positions). But the two are distinct; for example, it can be understood that a blood vessel may be accidentally misidentified even by an operator viewing a detailed model. Working from a partial model of anatomical geometry, anatomical identity may be still more ambiguous. Other information, for example as described herein, may augment and/or replace the use of anatomical geometry in establishing anatomical identity.

Unless otherwise indicated, anatomical identity is generally understood to refer to macroscopic anatomical structures (e.g., of a region being navigated by a catheter probe). These macroscopic structures optionally correspond to named anatomical parts. However, in some embodiments, anatomical identity is optionally made at least in part according to distinctions other than those of the standard anatomical nomenclature, which can be made from available data. For example, different anatomical identities may be assigned to regions with different tissue wall thicknesses, or other structural and/or positional differences which can be detected (e.g., by the use of dielectric measurements), but do not necessarily correlate with distinctions made by standard anatomical nomenclature.

An aspect of some embodiments of the present invention relates to automatic anatomical identification of an intrabody region based on combined inputs from a plurality of measurement sources.

In some embodiments, the plurality of measurement sources comprises at least one source giving positional information, and at least one source giving measurements of one or more properties which vary at different positions (e.g., electrical impedance at a position, and/or S-matrix describing an electrode array at the position). For example, a first source may give partial positional information, e.g., how far advanced a catheter is into a body, and/or what route a catheter used to reach its current location. Measurements from the second source may be used to determine position more specifically, with constraints applied to the determination based on the partial positional information of the first source.

An aspect of some embodiments of the present invention relates to the use of supervised machine learning to create one or more data structures useful in automatic anatomical identification of an intrabody region. A related aspect of some embodiments of the present invention relates to the provision of automatic indications of procedure actions to be performed in those regions.

In some embodiments, the one or more data structures include information describing anatomical variations (e.g., variation in numbers, sizes, local morphology, and/or relative positions of anatomical structures) which may be encountered during a procedure. Optionally, identification of one or more particular anatomical variations is further linked to automatic indication (e.g., recommendation) of procedure changes to potentially adapt procedure actions to the specific exigencies of an anatomical variation.

Some practitioners especially skilled in a procedure can identify intrabody regions, appropriate times, and/or alternatives for procedure actions with a high probability of success compared to peers. It would be of potential benefit to embed aspects of this skill in an automatic advisory system for use by less-skilled practitioners. In some procedures, for example, intervention procedures performed over catheter by indirect visualization, nearly all of the inputs (and many of the outputs) generated during a procedure are recorded in a digital form, which may capture substantially all the information which was available to a practitioner during performance of the procedure. This condition provides an opportunity for expert skill capture to an automatic system, based on supervised learning.

In some embodiments, the digital records of a plurality of catheter procedures are used, together with supervised machine learning, to produce an automatic advisory system linking different situational specifics to different suggested actions. For example, all data presented to a skilled practitioner before some procedure action (and/or during the procedure action) are treated as training inputs, while subsequent commanded movements and other actions are treated as feedback input which suggests what is to be done in response to the training inputs, when to do it, and/or to what degree to do it.

Optionally, in some embodiments, a skilled practitioner provides additional indications (narration, for example), describing features of their judgments and/or intentions which may not be inherently visible in their recorded actions. Optionally, procedure records (with or without supplementary annotations from a practitioner) are subjected to further markup before use in machine learning, for example to divide and/or label epochs within the procedure record, and/or to change the weighting of different aspects of recorded information (e.g., if the skilled practitioner has highlighted some feature during the procedure as important to decision making, and/or if there is some aspect of procedure action timing, extent and/or degree which should be a subject of particular focus for the machine learning). Optionally, post-procedure data (for example, procedure outcome results) are also provided as part of the machine learning input.

In some embodiments, machine learning is used to advise a procedure practitioner on the locations of heart structures. For example, in intervention to correct a defective heart valve, the atrial ventricular ring to which the mitral and the tricuspid valves are attached is a significant target. In some embodiments, a locatable intrabody probe (for example, a catheter probe) has at least one electrode. An AC current is injected from each electrode, optionally at a respective frequency, or otherwise distinguished, to allow separate identification of the electrodes used. The corresponding voltages generated on the same and/or other electrodes are recorded and processed by a Processing Unit (PU). These data can serve as input examples used within a learning data set (training data). Optionally, an expert practitioner provides feedback on the input examples by identifying signal recorded at certain positions as corresponding to a certain type of intra-body region, including target and non-target intrabody region; the latter being, an intrabody region excluded from being the subject of a certain procedure action. This identification can be implicit, for example, by actual actions performed or explicit, for example by tagging the recorded information. An implicit identification by actions may include, for example, identifying the fossa ovalis in a transseptal penetration, as the part selected for penetration by the skilled physician. Additionally or alternatively, the expert practitioner explicitly tags regions based on their own judgments.

In some embodiments, machine learning for this example uses input data in the matrices of the $S_{11}, S_{12} \ldots S_{ij}$ of the electrodes in different frequencies as well as the location of the probe relative to a known fiducial mark, or relative to an already identified region. An element $S_{ij}$ of an S matrix is a number, optionally a complex number, describing a ratio between an electrical field of a given frequency going through antenna i into the surroundings and an electrical field of the same frequency going at the same time through antenna j from the surroundings, when each antenna transmits an electrical field of a distinct frequency, e.g., in the radio frequency range of the electromagnetic spectrum. Optionally, the input data is provided for machine learning after normalization to correct for inter-patient variability. Expert actions and/or expert-provided observations provide the supervisory training feedback that relates the input data to particular cases, and serves as a basis for machine learning of association between input data and corresponding expert evaluations. After the machine learning result is validated as producing correct evaluations and/or action recommendations in response to data on parts of which the machine was trained, the learning result may be used to evaluate and/or recommend actions in response to new input.

An aspect of some embodiments of the present invention relates to providing of procedure guidance based on automatic anatomical identifications within an intrabody region.

In some embodiments, a procedure being guided comprises cryoablation. In some embodiments, a cryoballoon is used to ablate a closed line of tissue, for example, surrounding an entrance of a pulmonary vein to the left atrium. In some such embodiments, it is a potential advantage to have an indication of when the cryoballoon closes off flow through the pulmonary vein, since such blockage of flow potentially indicates that fully circumferential contact has been made by the balloon, so that a gap-free ablation line can be formed.

In some embodiments, procedure guidance includes detection (and indication to a user) of changes in sensed voltage by one or more electrodes located within a pulmonary vein as a cryoballoon configured for use in cryoablation closes off flow through the pulmonary vein.

Optionally, automatic procedure guidance is developed using techniques of machine learning. In some embodiments, experts indicate during a procedure, or during analysis of a replay of a procedure, when flow is blocked; and the machine learns relations between such indications and electrical potential readings. Results of the training may then be used to procedure guidance by following in real time changes in electrical potential detected by electrodes during a similar procedure carried out by a novice, and indicating when full blockage is achieved. In some embodiments, the system may be trained to identify actions to be taken once the flow blockage is achieved, and recommend these actions to the novice.

In some embodiments, a procedure being guided comprises penetrating the interatrial wall by an ablation catheter. In some embodiments, an electrode probe is passed over the interatrial wall while making dielectric measurements. Thinner walls are observed to have different dielectric properties than thicker walls. Optionally, position of thinning (or actual holes) near the center of the interatrial wall are treated as representing a target region across which an ablation probe is to penetrate the interatrial wall.

In some embodiments, a procedure to be guided comprises determining a location of a valve plane (e.g., in preparation for valvular treatment), and/or determining a location of an opening into the coronary sinus (e.g., in preparation for cannulation of the coronary sinus).

Optionally, automatic procedure guidance is developed using techniques of machine learning. In a learning stage, in some embodiments, an expert marks when a catheter is at a target position (e.g., the valve plane or the opening in the coronary sinus). The machine is trained to distinguish between readings of the electrodes at the target position and readings of the electrodes off the target positions. Then, in another procedure, the results of the training may be used to identify when the catheter is at the target position based on readings received from electrodes on the catheter.

For purposes of description, principles of the invention are described herein with respect to detailed embodiments relating to mapping of the cardiovascular system (or portions thereof) and/or navigation of an intrabody probe (e.g., a catheter probe) within a portion of a cardiovascular system. In some embodiments, the mapping and/or navigation is performed in the context of a cardiac intervention, for example: cardiac electrophysiological treatment, cardiac vascular treatment, and/or cardiac structural heart disease treatment (for example valvular treatments). It should be understood that in some embodiments, principles of the invention are applied, changed as necessary as may be understood based on the provided examples, to another medical intervention; for example: surgery, colonoscopy, biopsy, oncology surgery, orthopedic disk surgery, and/or plastic surgery.

Herein, a "map" (for example, as the term is used in relation to the act of "mapping") should be understood to be a machine readable data structure which describes a correspondence between values of a measurable position-dependent parameter, and the spatial positions at which those values are found by measurement. Using a map, knowledge that a certain parameter value is measured at a current (but potentially unknown) position can be used to help identify what the position is. The term should be understood to encompass maps instantiated, for example, as images, data tables, coordinate arrays, and/or mathematical functions. In some embodiments, a map also expresses spatial relationships among different positions, for example, adjacency, direction, and/or relative distance. An image, for example, is a map which indicates relationships of each of these sorts.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Method of Targeting and/or Action Selection by Anatomical Identification

Reference is now made to FIG. 1A, which schematically represents a method of automatic anatomical identification of a targeted intrabody region, and optionally automatic suggestion of a selected action on that target, according to some embodiments of the present disclosure. Reference is also made to FIG. 1C, which schematically represents a method of automatic anatomical identification of an intrabody region. Further reference is made to FIG. 1D, which schematically represents a method of automatic suggestion of a selected action on a target, according to some embodiments of the present disclosure.

At block 130, in some embodiments, the flowchart begins with selection of a target of a catheter operation. Inputs to block 130, in some embodiments, include operational context 210, measurement data 206, and anatomical schema 204A. These inputs to block 130 are also discussed in relation to other figures herein; in particular FIGS. 1B, 2A-2B, and 3A-3B. The output of block 130, in some embodiments, is a target selection 212A; wherein the target selection 212A selects from among targets defined in the anatomical schema 204A using the measurement data 206 and the operational context 210. The implementation of the selecting is largely governed by features of the data structure comprising anatomical schema 204A, which describe how operational context 210 and measurement data 206 are to be used, as now described in the following brief overviews.

Operational Contexts

In overview, operational context 210 comprises elements (or data indicative thereof) that may serve as background against which measurement data (e.g., measurement data measured using an intrabody probe) are interpreted. Elements of operational context 210 optionally include, for example:

system settings, positioning of an intrabody probe (e.g., positioning in a generally specified anatomical location, for example "in a left atrium", "in a right atrium", "in an aorta", "in a vena cava", "in the transverse colon", "in a bladder", or another anatomical location which is known from operational context data, but not as specific as the determination which is to be made using measurement data 206), state of an intrabody probe (e.g., operating state of an ablation probe, expansion state of an expandable and/or collapsible probe, and/or actuation state of a mechanically operated probe), status of a monitoring and/or control system supporting use of the intrabody probe, and/or the state of the patient undergoing the procedure.

Figure 2A:
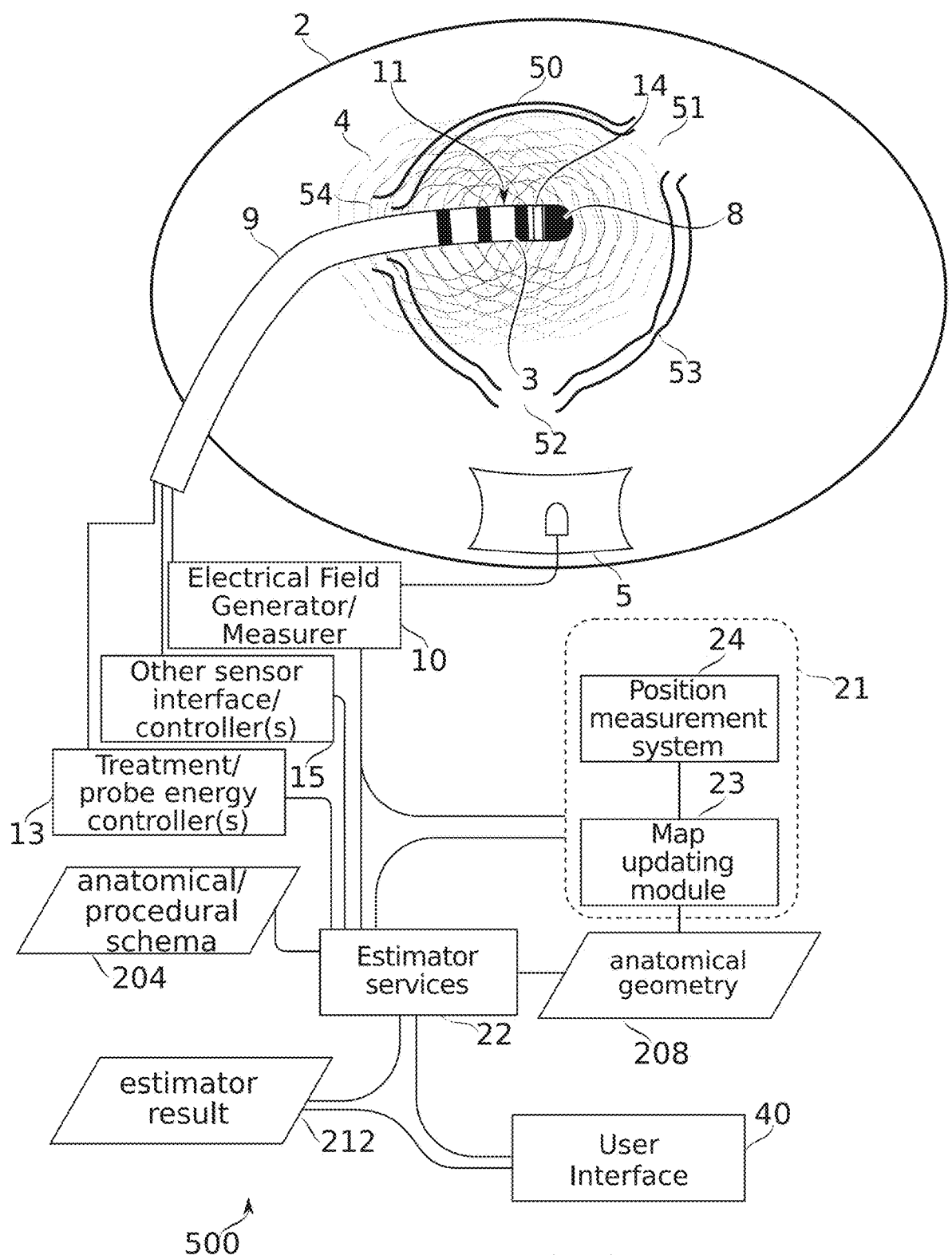
FIG. 2A schematically illustrates a system for use in performing the methods of FIGS. 1A-1B, including a schematic representation of a patient body, according to some embodiments of the present disclosure.

For example, operational context 210 corresponds, in some embodiments, to state of components in a system such as the one described in relation to FIG. 2A, herein. More particularly, operational context 210 may include data describing:

What procedure (e.g., a cardiac intervention procedure, for example a procedure to treat atrial fibrillation by ablation) is being performed, Where are (in general) elements of the catheter probe system and patient anatomy in relation to each other (for example "in the left atrium", "adjacent to the esophagus", or another a phrase, label, or categorization that indicates what parts of the patient anatomy are in the vicinity of the probe), In what state those elements are (e.g., operating state, expansion state, and/or actuation state), and/or What phase the procedure has reached.

In some embodiments, a system configured to carry out the method of FIG. 1A tracks operational context 210 continually during a procedure. Tracking may be based on progress through a procedure schema 204B, for example. In an example of such an embodiment, a system may set the operational context 210 to comprise readiness to perform a transseptal crossing upon detection of entry of the catheter into the vicinity (e.g., the lumen) of a right atrium.

Optionally, operational context 210 is set, at least in part, by explicit indications from a system operator (e.g., a physician). For example, when the operator is ready to begin a transseptal penetration, the operator optionally issues a command to the system to enter a transseptal penetration mode, which sets the new operational context 210 accordingly.

Measurement Data

In overview, measurement data 206 comprises available data which relates to the procedure underway, and is used to characterize measurement locations more specifically than the more general position characterization which may be performed using the operational context data in absence of measurement data.

In some embodiments, measurement data 206 relates to tracked positions (for example, electrically, magnetically and/or ultrasonically tracked positions) of a catheter probe, and/or measurements made using sensors and/or electrodes carried by the probe. The sensors may include, for example, force sensors and/or temperature sensors.

Electrical measurements may comprise, for example, voltage measurements in response to currents introduced through the same probe electrodes and/or different electrodes, such as other internally introduced electrodes and/or body surface electrodes. Optionally, electrical measurements comprise measurements of endogenous electrical activity of tissue near the catheter probe. Optionally, measurement data 206 comprise data related to measurements of tissue response (e.g., thermal and/or electrical response) during treatment activation, when the treatment activation includes, for example, activation of heating, cooling, injecting, irradiating, or otherwise therapeutically interacting with nearby tissue. Optionally or alternatively, measurement data 206 comprise data related to use of probing energies, such as irradiation, touching, or otherwise interacting with nearby tissue to probe the nearby tissue.

In some embodiments, measurement data 206 comprise any other data acquired and/or entered coordinate with operations of the procedure, including patient data (e.g., patient medical history, and/or vital statistics), patient monitoring data (e.g. heart rate, temperature, and/or respiratory rate), and/or previously or concurrently acquired imaging data (CT, MRI, nuclear, and/or X-ray images, for example).

In some embodiments, measurement data is of a location of a probe. The location may be recorded as absolute position and/or relative position. Optionally, location is recorded with respect to any suitable number of dimensions. For example spatial dimensions of a three-axis coordinate system may be recorded. Optionally, spatial dimensions are encoded indirectly, e.g., as position along a voltage and/or impedance gradient. Any number of gradients may be used, for example, gradients generated at different frequencies between a multiplicity of electrodes. Additionally/alternatively, time may be introduced as a dimension: linearly (elapsed time, for example), or cyclically (heartbeat phase and/or respiratory phase, for example). Optionally, location is recorded by use of one or more measurement values acting as a "tag" or signature of the location, for example, a set of impedance measurements. Optionally, other properties which may vary as a function of tissue environment are used; for example, any of the properties listed in the next paragraph.

In some embodiments, recorded data is of local tissue properties; for example: tissue thickness, molecular structure, IR reflectance, HoYag laser reflection, endocardial and/or other electrical activity, pH, and/or ion concentration. Optionally electrical measurements related to exogenously created electrical navigation fields, local electrical impedance, and/or local electrical reactance are treated as "local tissue properties".

In some embodiments, recorded data indicates a tissue change in some measured parameter such as impedance and/or temperature. For example, change of the measured parameter may be as a function of: probe pressure, heating, cooling, time per se, heartbeat phase, respiratory cycle, heart rate, defibrillation, and/or delivery of energy (which may be ablation energy or another kind of delivered energy, for example to temporarily inactivate tissue). Optionally, the change is monitored electrically from a probe electrode, for example as the change affects measurements of local impedance properties at one or more frequencies. Optionally, the monitored changing tissue property is directly related to the changed variable (for example, property of temperature is monitored for heating/cooling).

Anatomical Schema

In overview, an anatomical schema 204A comprises a data structure or collection of data structures defining rules. The rules relate a plurality of anatomical identities to one another (e.g., so that knowing the anatomical identity of a first structure gives information, under the rules, about what other anatomical structures are nearby that first structure), and/or relate characteristics of measurement data 206 to particular anatomical identities, at least within the operational context (which may include, for example, an anatomical location and/or a procedure phase) where the rule is relevant. Anatomical location may be a kind of location, described in reference to known landmarks (i.e., known anatomical name and/or function). Optionally, an anatomical schema 204A (or rule thereof) is defined for a particular operational context 210 and/or as a function of operational context 210. A schematic representation of an anatomical schema is described, for example, in relation to FIG. 3A.

Herein, the term "rule" is used to describe any function, equation, table, model, machine learning output, or other expression which can be evaluated together with some input to produce a result. Examples of results include a number, truth value, a selection from a range of options, a deductive conclusion, an inductive conclusion, and/or a statistical likelihood. Moreover, to be explicit: although certain types of machine learning results are sometimes described as expressing input/output associations without embodying distinct rules, herein such a machine learning result may nevertheless be considered, in and of itself, to embody at least a rule: that is, the rule of the expressed association that the machine learning result itself embodies.

As a partial example, again in the context of a procedure comprising transseptal penetration:
- an "interatrial septum" is optionally defined in an anatomical schema as comprising:
  - a "fossa ovalis"
  - wherein the fossa ovalis surrounded by regions (e.g., tracked positions in contact with wall tissue) which are "not fossa ovalis"; and
  - wherein a rule distinguishing between the "fossa ovalis" and "not fossa ovalis" operates on the basis of:
    - impedance measurement differences that correlate with wall thickness (the fossa ovalis being found over a thinner portion of the wall), and
    - optionally also on the basis of where the thinning is located (i.e., in a central region of the interatrial septum).

While the above description is presented in natural language for the sake of description, it should be understood that in some embodiments, a representation of an anatomical schema 204A for use in automatic processing is encoded in a suitable machine-readable format. Encoding optionally uses, for example, XML (e.g. according to a purpose-designed XML schema), JSON or another computer language-derived data structure description, a numerically encoded ("binary") format, weights for a neural network, another format suitable for encoding machine-learning derived algorithms, or in any other suitable format.

Relationships among regions of different anatomical identity which may be expressed by defined rules (explicitly by coding and/or implicitly by machine learning) in an anatomical schema 204A may include, for example, any one or more of the following, and/or their opposites as applicable:

Containing, being contained, comprising, or another relationship of "composition";

Adjacency, overlap, relative orientation, opposition (positions opposite one another within a lumen), relative distance, relative size or another relationship of spatial position and/or extent;

Co-occurrence, mutual exclusivity, and/or likelihood of either; and/or

Property correlations and/or relative values (e.g., co-variation and/or consistent relative magnitudes of lumen size, wall thickness, reactivity to stimulation, and/or susceptibility to edema).

In some embodiments, an anatomical schema 204A includes alternative rules which allow the anatomical schema 204A to encompass certain types of anatomical variability in a population. For example, in a normal population, potentially 75% of the population will have a fossa ovalis (a depression in the right atrium of the heart, at the level of the wall between right and left atrium, which is the remnant of a thin fibrous sheet that covered the foramen ovale during fetal development), and 25% of subjects will have a PFO (patent foramen ovale; that is, a full opening in the interatrial septum dividing the right and left atria, instead of a mere reduction in wall thickness). An anatomical schema may include rules to identify both characteristics of fossa ovalis and PFO. Other well-known variations in cardiac anatomy include but are not limited to:

Unusual persistence (and/or size) of the Eustachian valve which is normally only functional in fetal circulation, Numbers of pulmonary veins leading to the left atrium other than four (three, for example), and A relatively pronounced ridge between the pulmonary veins and the left atrial appendage (sometimes called a "warfarin ridge" for its resemblance in some diagnostic results to a thrombus, which may lead incorrectly to treatment with clot-thinning drugs).

It is noted that the rules of an anatomical schema 204A do not necessarily operate on the basis of precise descriptions of anatomical geometry (e.g., do not necessarily require reconstructions of tissue surfaces). They may do so, in some embodiments. In other embodiments, the rules of an anatomical schema 204A definitely do not operate on the basis of reconstructed tissue surfaces. Optionally, the rules operate on non-image data, and optionally not on image data.

Herein, image data are considered to be data arranged in a data structure that describes the value of a parameter at a multiplicity of physical spatial positions, according to a scheme that gives each described physical spatial position a definite and internally consistent distance and direction from the other described positions. Non-image data used in an anatomical schema optionally represent positions indefinitely—for example by the label of a general anatomical location, probabilistically (e.g., a range of likely relative distances), and/or according to threshold-defined ranges of distances. Optionally, non-image data represent positions according to parameter metrics which do not make use of physical position. As an example of non-image data: in some embodiments, anatomical schema 204A includes distributions of anatomical geometries, for example, data pertaining to the frequency at which certain distances between two anatomical landmarks may appear. In another example, anatomical schema 204A specifies locations by labels: for example, labels corresponding to phrase definitions like "in the left atrium", "adjacent to the esophagus". In a further example, anatomical schema 204A specifies categories which group anatomical locations (assigns them "logical labels"), but do not provide them with a definite spatial ordering.

Even if precise position data is available (for example, based on position tracking of a probe), use of comparison rules established by an anatomical schema 204A optionally ignores some or all of this precision. For example, it may not be relevant to a rule to know just how close to the center of the interatrial septum a candidate position for a fossa ovalis is, so long as, for example, it can be determined that there are a substantial number of distinguishable positions between it and regions with properties defining the outer boundaries of the interatrial septum.

Procedure Schema

At block 134, in some embodiments (FIG. 1C), the target selection 212A, selecting an intrabody region, is provided.

Optionally, the method of FIG. 1A continues at block 132. Alternatively or additionally, the method of FIG. 1D begins at block 132 with the receipt of information including target selection 212A. In FIG. 1D, target selection 212A is optionally produced as described in relation to FIG. 1A; or is otherwise provided; for example as a direct indication through a user interface, as an element defined along with procedure schema 204B, or from another source. The main difference from block 130 is that the selection operation of block 132 selects an action (output as selected action 212B), rather than an identification of a region.

Inputs to block 132, in some embodiments, include operational context 210, measurement data 206, and procedure schema 204B. Optionally anatomical schema 204A (e.g., the anatomical schema 204A used at block 130) is also included as input. However, procedure schema 204B may itself be understood as a particular type of anatomical schema 204A defined as a data structure comprising rules, in which the rules that relate and characterize different anatomical identities are also provided with indications (derived from rules applied to inputs) of what actions should be performed on regions having those anatomical identities in the context of a particular procedure and/or phase of a procedure. Herein discussions of aspects of an anatomical schema 204A should be understood to apply also to a procedure schema 204B, except as otherwise noted.

For example, the action associated with a PFO in a procedure schema 204B may simply be to pass a catheter probe through the open hole, while the action associated with a closed fossa ovalis may be to penetrate it by needle and/or the use of an ablation probe. In this case, the identity of the target selection 212A of an intrabody region (open or closed hole) interacts with the operational context 210 (transseptal penetration) to select alternate options encoded by the procedure schema 204B. In some embodiments, the selected action 212B is subject to more detailed control—for example, if an ablation-assisted transseptal crossing is selected, the selected action 212B optionally comprises specification of ablation parameters to be used, which may vary, for example, based on the measured and/or anticipated thickness of the fossa ovalis.

In some embodiments, selected action 212B is provided as an indication to an operator which may be treated by the operator as an option, suggestion, and/or recommendation. In some embodiments, selected action 212B is automatically used by a system to set parameters for the next operation (optionally while maintaining an available option for the operator to override the parameters. In some embodiments, selected action 212B is begun automatically by the system as soon as some criterion is met—for example, ablation is optionally begun (e.g., with prior operator permission) as soon as the system reaches some predetermined degree of confidence that the catheter probe is currently in contact with the true fossa ovalis.

Target/Action Selection within a Procedure

Figure 1B:
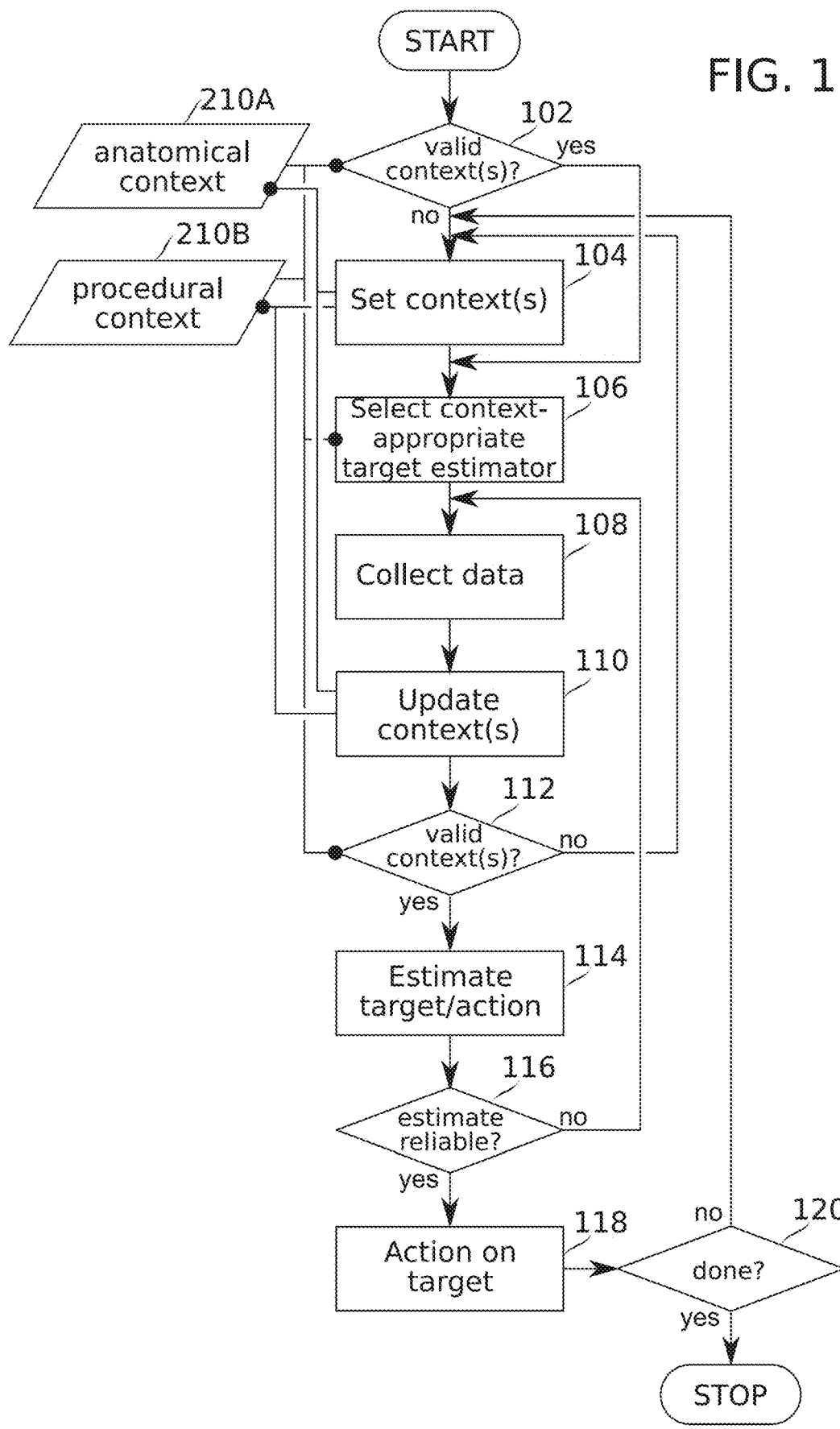
FIG. 1B is a schematic flowchart of the use the method of FIG. 1A within the context of a procedure, according to some embodiments of the present disclosure.
Figure 1C:
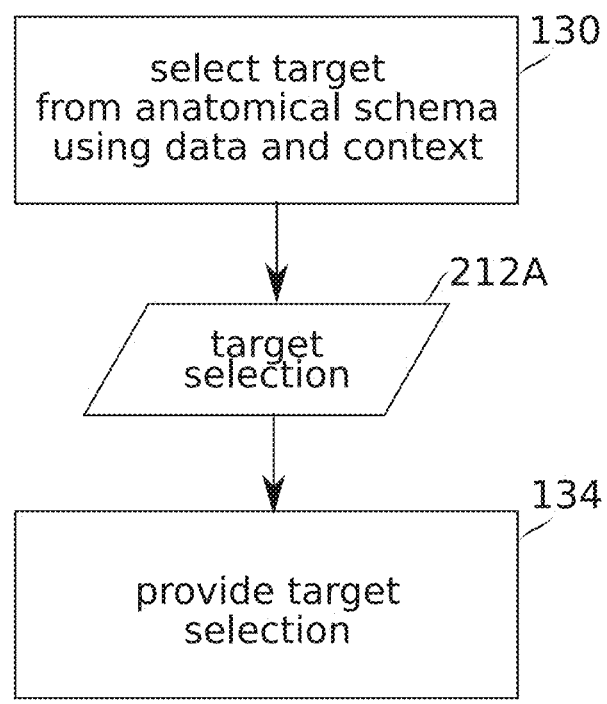
FIG. 1C schematically represents a method of automatic anatomical identification of an intrabody region, according to some embodiments of the present disclosure.
Figure 1D:
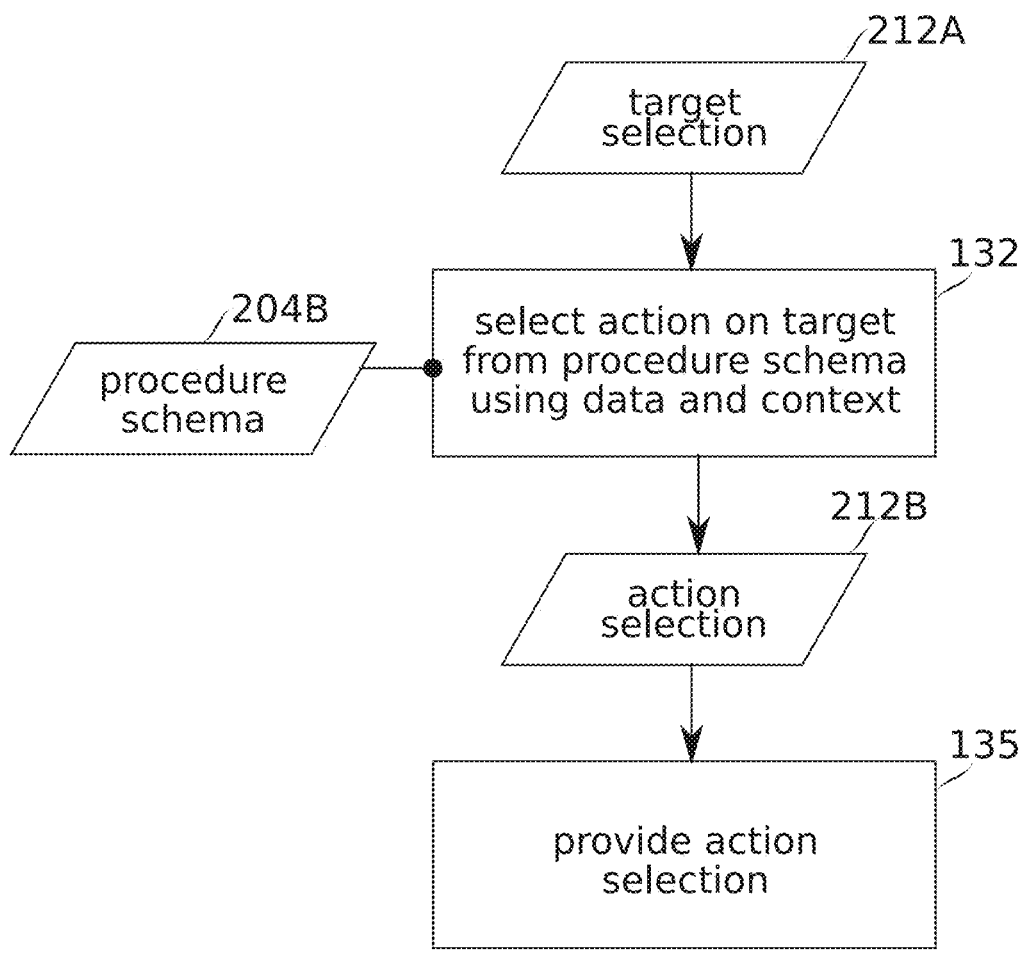
FIG. 1D schematically represents a method of automatic suggestion of a selected action on a target, according to some embodiments of the present disclosure.

Reference is now made to FIG. 1B, which is a schematic flowchart of the use the method of FIG. 1A within the context of a procedure, according to some embodiments of the present disclosure.

In some embodiments, a target action is to be performed on some targeted intrabody region. It is referred to as "target action", since an intended (targeted) result and/or a general class of planned action may be known, with how to accomplish that result and/or how to preferably carry out the planned action at least partially to be determined. At block 102, in some embodiments, a determination is made as to whether there is currently available a valid procedural context based on which further processing can proceed. A "valid" procedural context is one that is appropriate to the target action, and sufficiently well-characterized as to allow planning and performing the target action. If yes, the flowchart continues at block 106. Otherwise, flow continues to block 104, at which a context is set.

FIG. 1B introduces an optional distinction between two aspects of operational context 210—anatomical context 210A and procedural context 210B. There need not be a sharp distinction implemented between these two. At least for purposes of description, however, anatomical context 210A may be understood to comprise information describing the "where" of the current context—for example, where a catheter probe is located, and/or where a current target intrabody region of the catheter (e.g., a region targeted for ablation) is located. Procedural context 210B describes the "what" of the current context, for example, what a goal of a current phase of a procedure is (or other features of the current procedure phase). Optionally the two types of context are intermingled in their use and/or definition. Optionally, only one of the context types is used and/or defined. For example, in a defined procedural context, all information about anatomical context is optionally subservient to "what to do next". An interatrial septum, for example, is optionally treated as only relevant during the phase of the procedure where it becomes a target intrabody region for the target action of crossing it. This perspective optionally allows taking a focused approach to defining "context", which has the potential advantage of controlling complexity. On the other hand, the approach can be brittle, since if a procedure leaves the main path of the procedure (e.g., by accident), there may not be a well-defined way to guide a return.

"Setting" a context 210A and/or 210B is optionally manual, automatic, or a blend of the two. An example of manual context setting is to simply have a user inform a system, e.g., that the procedure is now in some particular phase (related to procedural context 210B), a catheter is now in some particular place (related to anatomical context 210A), and/or a particular goal of the current phase has now been reached (again, more related to procedural context 210B). Then the system can set a new context, based on that input. The input can be, for example, via user interface 40, for example as described in relation to FIG. 2A.

In an example of automatic context setting, a system is optionally configured to recognize a context based on automatically acquired measurement data 206 (for example, but not necessarily, in conjunction with the use of one or more rules of an anatomical schema 204A). For example, after sufficient exploration of a right atrium (without necessarily knowing that it is a right atrium), a system optionally has available to it sufficient information to constrain a catheter probe as being within a chamber of a certain minimum size, and connected to two large, oppositely situated blood vessels. Optionally, a rule of an anatomical schema 204A is defined so that these characteristics uniquely (or at least probabilistically) indicate that the probe is indeed located within a right atrium. Optionally (for example, based on the location of the probe, its entry point, and the positions of the two blood vessels), the system is also able to determine in what direction from the probe lay other potential target features of the right atrium. Such features could be, for example, the interatrial septum, the opening into the coronary sinus, and/or the plane of the tricuspid valve. In some embodiments, manually provided "seed" context is used to orient the system, after which acquired data are matched to suitable anatomical identities defined by application of rules of the anatomical schema 204A based on sequential encounters during a procedure. For example, catheters passing in from the jugular vein or the femoral vein should enter the heart itself in different locations, so that data indicating entry to a heart chamber would be interpreted differently in each case.

At block 106, in some embodiments, a target estimator (which may be considered as a type of rule defined by an anatomical schema 204A) is selected based on the contexts (anatomical and procedural). This selection of an estimator may be one of the operations performed in block 130 of FIG. 1A. That is, the target intrabody region may be selected in block 130 of FIG. 1A using the estimator selected at block 106 of FIG. 1B. In some embodiments of the invention, the types of measurement data 206 used in target intrabody region selection, as well as how that data is used, can be very different depending on the current context. From an operational context within the right atrium, for example, an estimator for finding the entry to the coronary sinus (as a target intrabody region) should look for different characteristics than an estimator for finding the fossa ovalis (as a different target intrabody region). Knowing the current anatomical and procedural context 210A, 210B (in this case, it is procedural context 210B that is distinguishing) potentially allows the correct estimator to be selected.

At block 108, in some embodiments, data (that is, data corresponding to measurement data 206) is collected, for example as a catheter probe is moved around within the general vicinity of the target tissue region being sought. As data is collected, it is possible that the operational context will change (intentionally or by accident); so at block 110, operational context is periodically updated based on the same measurement data 206. At block 112, if the operational context is no longer valid for the current target estimator (appropriate to the target action, and sufficiently well-characterized as to allow operation of the estimator), flow returns to block 104, where a new operational context is determined (or verified), and that part of the process begins again. Otherwise, at block 114, the estimator selected at block 106 is used in an attempt to estimate where the current target is and/or what specific target action to take (as appropriate).

The estimate attempt may or may not succeed; for example, there may be insufficient data to make a good early estimate. At block 116, a determination is made as to whether the estimate result should be treated as reliable. If not, more data is collected at block 108. Otherwise, the flowchart proceeds to block 118, at which an action on a target is made. Either the action, the target, or both may be specified from the results of block 114 (with the operator tacitly responsible for accepting the specification of ablation parameters to be used, and supplying whatever detail may be missing from the specification).

At block 120, a determination is made as to whether the procedure has completed or not. If not, flow returns to block 104, at which a new context is potentially set. Otherwise, the flowchart ends.

Examples of System Embodiments

System Overview

Reference is now made to FIG. 2A, which schematically illustrates a system 500 for use in performing the methods of FIGS. 1A-1B, including a schematic representation of a patient body 2, according to some embodiments of the present disclosure.

At the core of system 500 (for purposes of the present descriptions) is a block representing estimator services 22. This block is described in more detail in relation to FIG. 2B. The estimator services are optionally implemented by a computer processor programmed to accept inputs and provide outputs as described, for example, in relation to FIGS. 1A-1B and/or 2B. In some embodiments, inputs to estimator services 22 comprise anatomical/procedure schema 204 (which may comprise one or both of anatomical schema 204A, and procedure schema 204B). The other connections leading into estimate services 22 comprise examples of various sources of measurement data 206.

As an input to estimator services 22, user interface 40 may be used to set context and provide other user-generated selection data, for example as described in relation to block 104 of FIG. 1B. User interface 40 also functions as an output for, among other functions the system may require, indications provided as estimator results 212 of estimator services 22 (e.g., target selection 212A and/or selected action 212B of FIG. 1A).

Figure 2B:
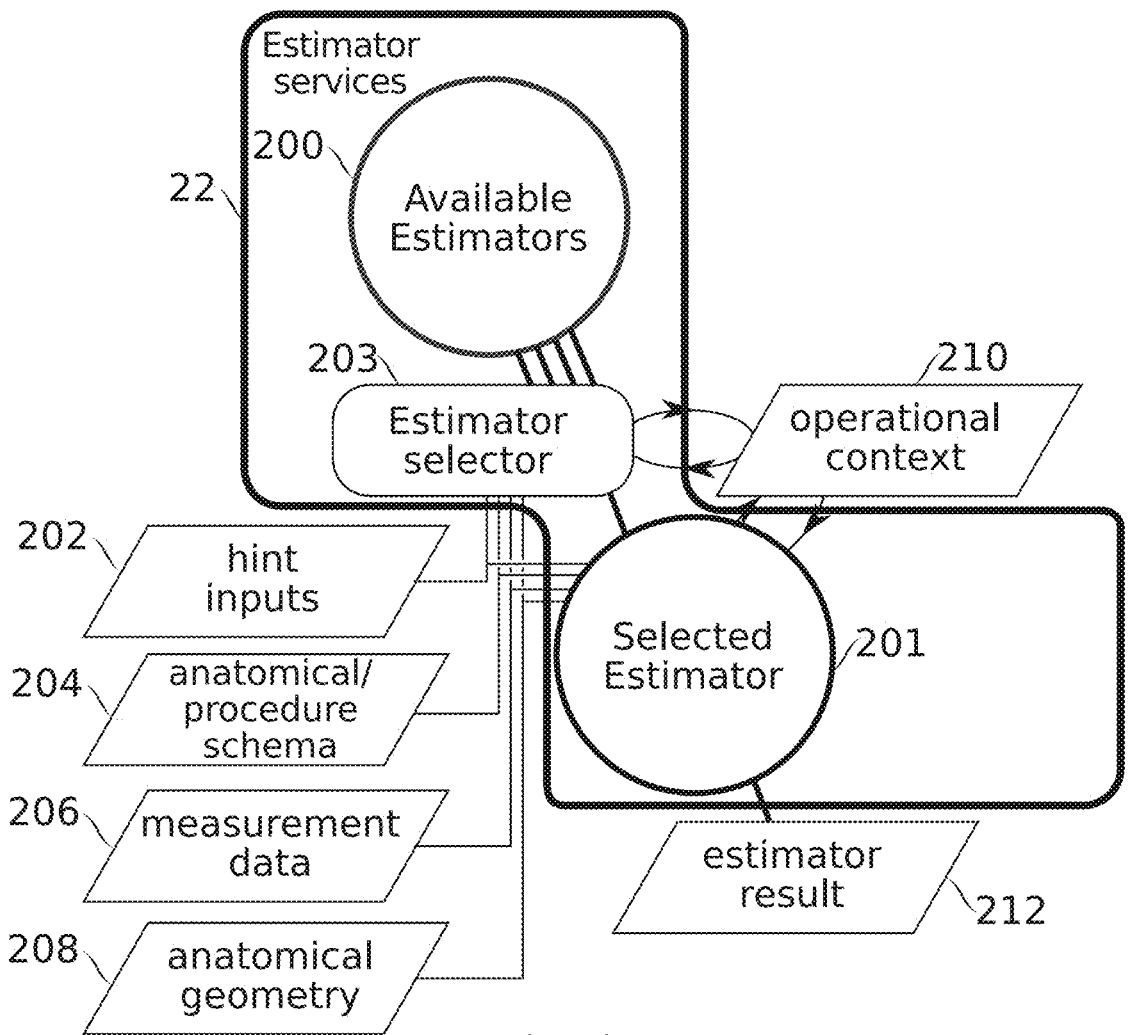
FIG. 2B schematically represents inputs and operations of an estimator services module, according to some embodiments of the present disclosure.

Other inputs provided to estimator services 22 shown in FIG. 2B emphasize the role of an intrabody probe 11 of a catheter 9 in sensing various parameters for use in the operations of estimator services 22. It is to be understood that other input sources are optionally used; for example, as described in relation to block 206 of FIG. 1A. Electrical field generator/measurer 10 is provided as a general purpose block covering all electrical sensing functions. Optionally, it is implemented as a plurality of sub-modules. In some embodiments, a major function of electrical field generator/measurer is to generate and sense electrical fields 4 for use in navigation, for example, using pairs (and/or other configurations) of body surface electrodes 5 (only one body surface electrode is shown in the schematic drawing). In some embodiments, navigation comprises detecting voltages using electrodes 3 of probe 11 as they move through a plurality of crossed (e.g., approximately orthogonal) time-varying (e.g., at radio frequency) electrical fields. Each voltage is distinguished, for example, on the basis of frequency. Optionally, the crossed fields are treated as coordinate axes, optionally transformed as necessary to produce 3-D spatial coordinates. While body surface electrode-generated fields are used in FIG. 2A as an example, fields used for electrical navigation are optionally produced from other sources; for example, from intrabody electrodes located near a body cavity 50 to be navigated (e.g., in the coronary sinus for coronary navigation requirements). Optionally, the electrodes of probe 11 itself are used to both produce and sense electrical fields, and the sensed voltages treated more as "tags" characterizing different locations than as coordinates on coordinate axes.

In some embodiments, measurements made by electrical field generator/measurer 10 are relayed to position services module 21 (optionally implemented as software running on a processor). By whatever method is appropriate to the configuration of the system, position measurement system 24 converts the voltage measurements from the probe into probe positions, while map updating module 23 uses these positions to generate a map of the body cavities which probe 11 navigates. Over the course of a procedure, and in particular for regions which probe 11 visits exhaustively, there may be a highly detailed map generated. However, this condition of dense visitation potentially does not hold (and/or holds at the cost of inconvenience and procedure delay) for all regions, and anyway there is potentially a significant period of time that passes before high-resolution map is available. Nevertheless, the positions and maps created and/or maintained by position services module 21 are provided as inputs to estimator service module 22, in some embodiments, as a source of data on which target and/or action estimators operate. Optionally, but not necessarily, this data is provided in the form of a current best estimate of anatomical geometry 208. Optionally, anatomical geometry 208 is estimated based on results of a prior catheterization procedure. Optionally, anatomical geometry 208 is estimated at least in part and/or initially based on currently or previously acquired imaging data, for example, imaging by CT, MRI, NM, ultrasound, X-ray, or another imaging technique. Optionally, anatomical geometry is estimated at least in part and/or initially based on anatomical atlas information.

The data produced by electrical field generator/measurer 10 optionally include data other than that which serves as a direct basis for measured spatial position navigation. In particular, electrodes 3 may be operated to obtain data influenced by the local electrical environment of tissue, for example dielectric property data; or more generally, differences in impedance or other basic electrical properties as a function of local tissue environment. Two types of anatomical features which are particularly distinguishable from such data are approaches of an electrode probe 11 to tissue walls, and the relative thickness of those walls as electrode probe 11 moves along them. This allows distinguishing, for example, more confined cavities (e.g., passages into/out of body cavity apertures 51, 52, 54) from more open cavities, and thicker walls from thinner ones (e.g., thin wall feature 53). Such electrical properties and their uses are described in connection with embodiments of specific applications described herein, for example, in relation to FIGS. 4A-4C, 5, 6, 7A-7B, 8, 9A-9D, 10A-10B, and 11 herein.

In some embodiments, one or more non-electrode sensors 14 is optionally provided, either as an integral part of probe 11 (as shown), or as part of an auxiliary probe used with it. Such a sensor may comprise, for example, a force and/or temperature sensor. Data from such sensors is optionally collected by other sensor interface controller(s) 15, and provided to estimator services 22 as another form of input.

In some embodiments of the invention, probe 11 comprises one or more elements 8 supporting one or more treatment modalities. Examples include elements for cryoablation (balloon and fluid conduits, for example), one or more RF ablation electrodes, injectable substances and their injection means (needle), or another treatment modality. In some embodiments, details of the operation of treatment probe energy controller(s) 13 are provided to estimator services 22, for example to assist in the evaluation of changes produced as a result of manipulation via element 8. Optionally, treatment parameters' under the control of controller 13 are controlled and/or suggested based on outputs from estimator services 22 (for example, in embodiments where an output of estimator services 22 comprises parameters of a selected action 212B).

Estimator Services

Reference is now made to FIG. 2B, which schematically represents inputs and operations of an estimator services module 22, according to some embodiments of the present disclosure.

In some embodiments, inputs to estimator service module 22 include hint inputs 202, anatomical/procedure schema 204, measurement data 206, and/or anatomical geometry 208.

In some embodiments, hint inputs 202 comprise one or more forms of non-measurement data which are used by estimator services 22 in setting context which may help in selecting an estimator (for example as described in relation to block 104 of FIG. 1B), and/or provide information used by an estimator (e.g., information used by selected estimator 201) to produce an estimator result 212. In some embodiments the hint inputs comprise explicitly provided inputs from an operator, for example, inputs specifying a location of probe 11, a port of entry of probe 11, which probe 11 of an optional plurality of probes is being used, operational phase of a current procedure, a selection among potential anatomical variants, or another input.

In some embodiments, hint inputs 202 comprise information implicit to the choice of system configuration and/or procedure. For example, estimators which rely on electrical field navigation-type position inputs are normally unavailable for selection by estimator selector 203 if electrical field navigation is not being used. Hints can also include, for example, specification of the point of initial access of a catheter to a body (e.g., femoral vein or jugular vein) and/or details of anatomy (for example, the presence of variant anatomy structures) which may be known from previous data such as prior catheterization and/or imaging procedures.

Figure 3A:
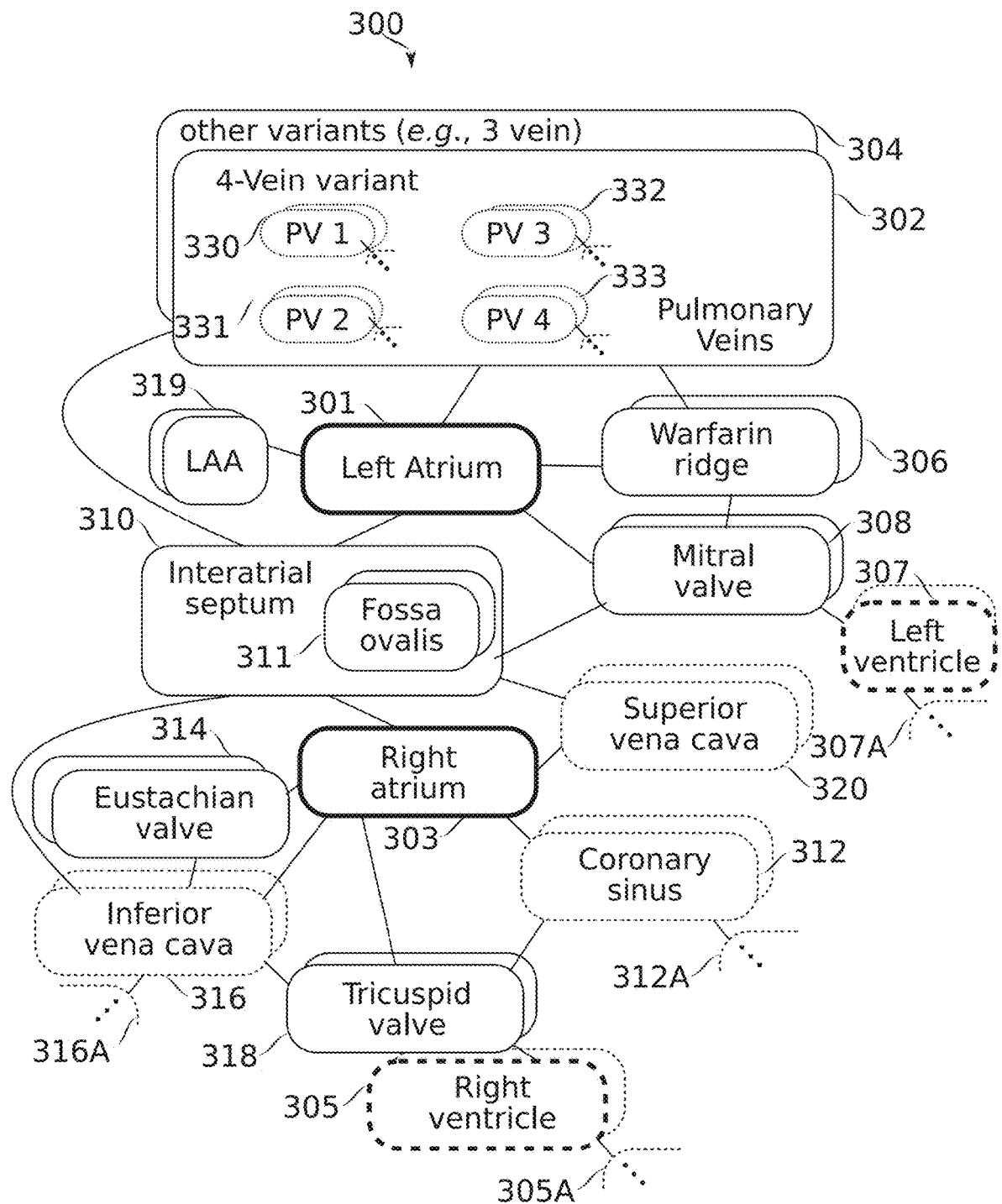
FIG. 3A schematically represents selected anatomical relationships encoded by an anatomical schema, according to some embodiments of the present disclosure.

Anatomical/procedure schema 204, in some embodiments, comprises one or more rule-defining data structures configured as described, for example, in relation to FIG. 1A, and/or as described in relation to the schematic example of FIG. 3A.

Measurement data 206, in some embodiments, comprises data from one or more sources of measurements, for example one of the sources listed in relation to block 206 of FIG. 1A, and/or described in relation to the various data collecting elements (e.g., electrical field generator/measurer 10, other sensor interface/controller(s) 15, treatment probe energy controllers 13, and/or position measurement system 24) of FIG. 2A.

Anatomical geometry 208, in some embodiments, comprises a current estimate of patient anatomy in a region of interest, for example as described in relation to block 204 of FIG. 2A.

In some embodiments, estimator services 22 comprises two main operations: (1) selection of an estimator 201 by an estimator selector module 203 from among a pool of available estimators 200, and (2) use of the selected estimator 201 to produce an estimator result 212, based on currently available inputs. These operations are described, for example, in relation to FIG. 1B. It is noted that in some embodiments there is also maintained by the estimator services 22 an operational context 210, comprising one or both of a current anatomical context and a procedural context.

Examples of Anatomical Schema

Figure 3B:
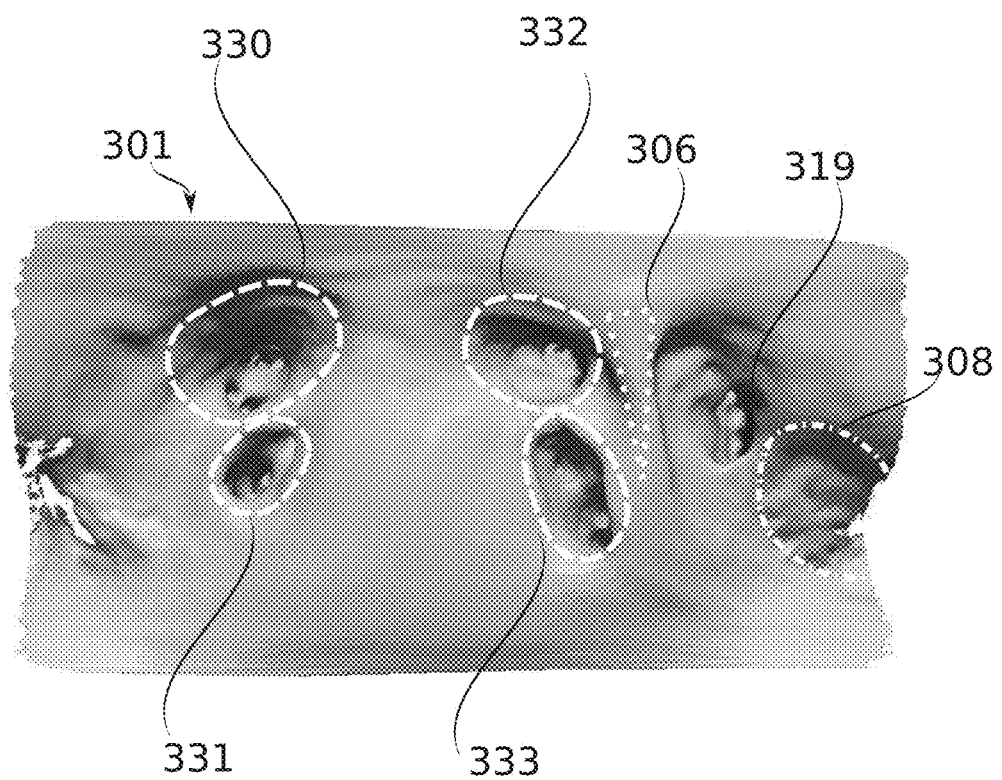
FIG. 3B illustrates some of the left atrium features mentioned in FIG. 3A in an "unwrapped" view of the left atrium, according to some embodiments of the present disclosure.

Reference is now made to FIG. 3A, which schematically represents selected anatomical relationships encoded by rules of an anatomical schema 204A, according to some embodiments of the present disclosure. Reference is also made to FIG. 3B, which illustrates some of the left atrium 301 features mentioned in FIG. 3A in an "unwrapped" view of the left atrium, according to some embodiments of the present disclosure.

The portion of the anatomical schema 204A illustrated in FIG. 3A emphasizes relationships among regions of different anatomical identities that relate to the atrial chambers of the heart (that is, rules governing aspects of their spatial relationships to one another). It is to be understood that the diagram of FIG. 3A is a visual representation of logical relationships which would normally be otherwise encoded (e.g., as XML, JSON, and/or a binary format), for example as described in relation to block 204A of FIG. 1A. Elements of the diagram illustrate examples of features mentioned in that description, for example relationships of position and composition. Selected examples of the use of property features are also discussed below in relation to particular anatomical identities.

In some embodiments, an anatomical schema 204A may include coverage of all or any suitable fragment of the anatomical structures shown in FIG. 3A, and optionally different or additional anatomical structures. Potential advantages of a more complete anatomical schema 204A include coverage of more situations (e.g., more navigation regions, different available data, more types of anatomical variants), and/or increased reliability of automatic inferences made using rules of the schema (e.g., because more lines of evidence potentially converge to confirm an identification of a target intrabody region). A more complete anatomical schema 204A may also be useful for uninterrupted control and/or monitoring of the flow of operations throughout a larger section of the overall procedure, for example for support of multi-chamber operations. In contrast, a relatively fragmented anatomical schema may still be of value for providing assistance during particularly difficult and/or error-prone phases of a procedure. For example, a fragmented anatomical schema may comprise just rules for identifying a fossa ovalis target within an interatrial septum, assuming prior localization of the interatrial septum. As previously noted, a procedure schema 204B is optionally implemented as a narrowly defined anatomical schema, wherein each anatomical identity in the schema is provided with information particularly tailored to progressing the procedure from one phase to the next. Optionally, identities shown in FIG. 3A as "anatomical identities" are recast as "procedural identities", focusing on phases of navigation and/or intervention such as "enter right atrium", "cross the IAS", "ablate" and the like—in this case, anatomical identities are optionally entities subservient to the exigencies of each sequential operational phase of the procedure.

For brevity, in the descriptions of FIG. 3A that follow, schema entries comprising collections of rules for particular anatomical structures (anatomical identities) are referred to by common names for those anatomical structures. However, it should be understood that such references with respect to FIG. 3A are actually to the portion of the anatomical schema data structure that pertains to the actual anatomical structure mentioned, not the anatomical structure itself.

Beginning with schema entry for the right atrium 303, FIG. 3A shows that the right atrium 303 is directly connected to typical and/or variant right atrium features such as tricuspid valve 318 (leading to the right ventricle 305), inferior vena cava 316, coronary sinus 312, superior vena cava 320, interatrial septum 301, and Eustachian valve 314. This list of connected elements is not necessarily exhaustive, and any given implementation of an anatomical schema optionally adds or removes schema entries as appropriate for the particular procedure(s) which are to be supported. Several of the schema entries of FIG. 3A are indicated with doubled overlapping enclosures. This is to indicate the optional presence of variant anatomies, the detection and encoding of which is described herein with respect to some selected examples. Another convention of FIG. 3A is the use of partial boxes to indicate the optional inclusion in some embodiments of additional schema entries not shown in FIG. 3A, for example unnamed features 305A, 312A, 307A, and 316A, connected their correspondingly numbered (without the terminal "A") anchoring schema entries.

One example of an anatomical variant is Eustachian valve 314, a valve of the inferior vena cava (IVC) which is large in the fetal stage, and plays an important role in fetal circulation as it directs oxygenated blood from the maternal placenta directly across the patent foramen ovalis into the left atrium thereby reaching the left ventricle (avoiding the lungs) and being pumped, e.g., to the brain. In some embodiments, the maintained and/or enlarged presence of this valve in an adult patient is associated with increased risk of right to left paradoxical shunt of emboli across the PFO (stroke). In some embodiments of an anatomical schema, a criterion for noting the presence of an enlarged Eustachian valve comprises a finding of interference with movements and/or positioning of a probe 11 in the region of the IVC (particularly compared to the superior vena cava, SVC). In some embodiments, such a criterion comprises a finding of otherwise unexpected fluctuations in impedance properties consistent with contact with a wall or flap, in a place where a canonical anatomy would be free of such fluctuations. Meeting one or both of these criteria in a certain location optionally not only sets that location "Eustachian valve", but also helps to identify a nearby region having, for example, impedance and/or navigationally restricting features of a blood vessel inlet as being more specifically the inlet to the right atrium of the IVC. This in turn allows the deductive inference that a second such blood vessel inlet is the SVC. From this the orientation of the right atrium is now known, allowing localization of the direction in which the interatrial septum 310 lies, and, at least along the IVC/SVC axis, something about its extent. Similarly, the general position of features such as the coronary sinus and tricuspid valve can be automatically deduced (crossing the tricuspid valve, for example, is optionally noted from changes in intra-cardiac ECG), and any "sinus like" or "valve like" features in those positions assigned to be actually the appropriate feature with a high degree of confidence.

Similar chains of deduction can be built up from different starting points and/or hints. For example, if it is known that the catheterization procedure began from a femoral vein, then the IVC/SVC distinction can be inferred based on the vein-like aperture, through which the catheter first enters the right atrium. Entry to the right atrium itself may be detected by such features as how many and/or what relative size of apertures lead from it (once it is mapped to sufficient completeness), how far a probe can move across it in one or more directions before encountering impedance changes characteristic of a wall encounter, an impedance reading while in the heart chamber which indicates that all tissue walls are far away, impedance or other electrical readings which show a pronounced heartbeat cycle-dependent fluctuation, detection of electrical impulses propagating through the walls of the chamber, and/or another distinguishing property of the right atrial chamber environment measurable by a probe situated therein. Any or all of these types of measurement-based indications and/or logical deductions are optionally provided as explicitly encoded features of an anatomical schema 204A. However, in some embodiments, some or all of these indications and/or logical deductions are found and encoded implicitly, for example based on supervised machine learning techniques, for example as described in relation to FIG. 3C.

Figure 5:
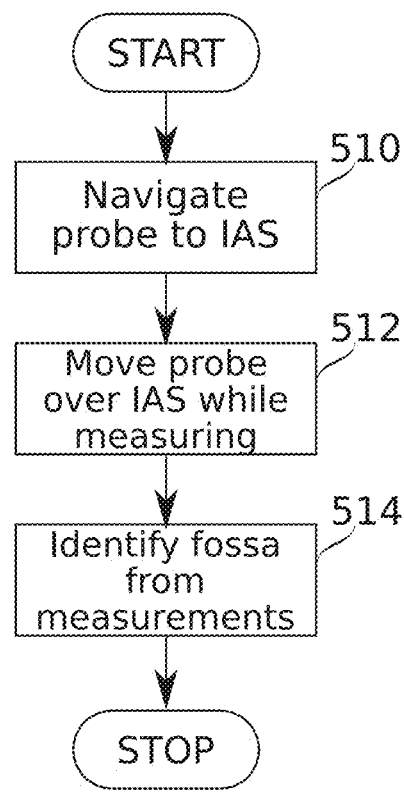
FIG. 5 is a schematic flowchart describing a method of locating a fossa ovalis, according to some embodiments of the present disclosure.

Another situation for which an anatomical schema may provide guidance is in the location of a fossa ovalis (or PFO), for example as described in relation to FIG. 5, herein. With respect to the structure of the anatomical schema, it is noted for now that the fossa ovalis 311 is optionally encoded as an anatomical sub-identity of the interatrial septum 310. For purposes of locating the actual fossa ovalis, a search strategy optionally proceeds first by finding some part of the interatrial septum, and then by further search locating the fossa ovalis 311 itself.

Continuing from the schema entry for the fossa ovalis 311, the anatomical schema of FIG. 3A also comprise a schema entry for left atrium 301. Visual appearances of some of these features can be seen in an unwrapped view of the internal lumenal surface of a left atrium shown in FIG. 3B (in FIG. 3B, reference characters label anatomical features as such using the same numbering scheme applied to the anatomical names applied more narrowly to schema entries in the descriptions of FIG. 3A).

In addition to the fossa ovalis 311 and interatrial septum 310, left atrium 301 is also connected to several other features which line (or may line) its interior lumenal wall, including the left atrial appendage (LAA) 319, the pulmonary veins 302, the so-called (and optionally present in variant forms of various sizes) warfarin ridge 306, and the mitral valve 308 (which leads to the left ventricle 307, which has not been detailed in the figure).

Of particular interest as an example is the potentially variant anatomy of the pulmonary veins, which can potentially be present as the canonical 4-vein variant (pulmonary veins (PV) 330, 331, 332, 333), or in another variant form 304 such as a three-vein variant. In some embodiments, an anatomical schema is adapted to automatically select from among possible variants based on numbers of aperture features actually encountered, and/or based on where aperture features are encountered (for example, encountering an unusually large ostium in a position intermediate to the canonical four-vein positions of two PVs is optionally treated as evidence that the three-vein anatomical variant of the anatomical schema should be used.

Thus, each schema entry for a certain anatomical identity is optionally locatable based on at least one of the following types of information:

How it is positioned and/or oriented with respect to other identified anatomy parts;

How it is positioned and/or oriented with respect to a probe being used in the procedure;

What sorts of properties (for example, impedance properties, or any other property for example as described in relation to FIG. 1A) it is expected to have (even if those properties as such are only partially identifying, they may work together with information about the overall anatomical context to form a full positive identification)

What sorts of properties help to distinguish relevant anatomical variants from one another.

In some embodiments, as different regions of an anatomy are automatically provided with anatomical identities, a system indicates these identities to a user through user interface 40. Optionally, anatomical identities (previously and/or currently provided as target selection 212A, for example) are associated with a degree of confidence, which potentially may be increased by the acquisition of additional data. Optionally, indications can be manually set by system operators. Optionally, automatically determined indications can be edited and/or overridden by system operators. Manual identification input may be used, for example, as supervised results paired with training data collected for use in machine learning of associations that produce target and/or action estimator results 212 from input measurement data 206.

In some embodiments, anatomical identities are shown on user interface 40 as tags, for example, character abbreviation tags, colored spheres (with associated dictionary), fully colored and/or textured regions of anatomical surfaces (e.g. heart chamber and/or vascular wall), shading effects to simulate surface features (e.g., bump mapping to highlight an identified region of a fossa ovalis), and/or special lighting effects applied to a rendered view approximating the anatomical geometry. For example, lighting may be simulated within the PVs and/or atrial-ventricular valve planes to mimic the color Doppler scheme according to direction of blood flow (e.g. blue-away, red-towards, or another convention). Optionally, tags that apply to hidden surfaces (for example, coronary sinus ostia) are visualized by, for example, changing the opacity with which an anatomical geometry is displayed, and/or applying a clipping plane to the display. Optionally, tag display effects are modulated to indicate confidence, for example, made more transparent, less saturated in color, differently textured, made more diffuse, or otherwise modified. Optionally, confidence is simply displayed as graphical indications like bars, dots, and/or numbers.

Actions (for example, selected action 210B) selected on (e.g. recommended for) a target region are optionally signaled by arrows, glowing and/or pulsing markers, or other signals. Certain types of actions are typically accompanied by changes in shape or position which can be inferred from non-imaging readings. For example, crossing of the fossa ovalis may be accompanied by characteristic "tenting" for example as described in relation to FIGS. 4A-4B. In some embodiments, these changes are simulated in a display for the user, wherein the simulation is synthesized on the basis of available non-imaging data.

Machine Learning Results Used with Anatomical Schema

Figure 3C:
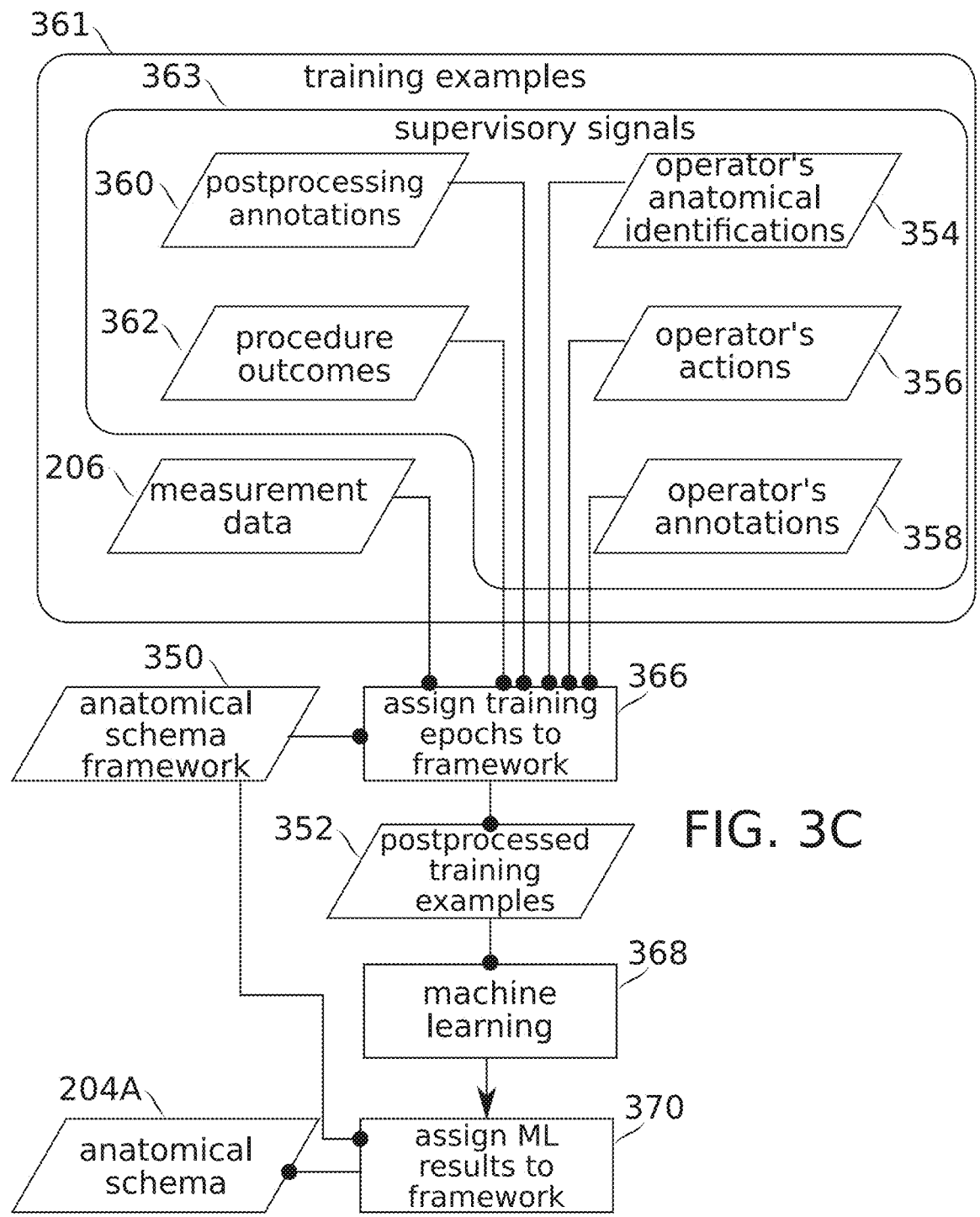
FIG. 3C is a schematic flowchart of the use of machine learning to establish at least some aspects of an anatomical schema, according to some embodiments of the present disclosure.

Reference is now made to FIG. 3C, which is a schematic flowchart of the use of machine learning to establish at least some aspects of an anatomical schema 204A, according to some embodiments of the present disclosure.

Supervised machine learning comprises a family of techniques known in the art which are applicable to infer a function from a set of training examples (for example, training examples 361 of FIG. 3C). The training examples include pairs of inputs and their expected outputs (the outputs are provided as supervisory signals, for example supervisory signals 363 of FIG. 3C). The result of the machine learning is a function or other data structure which can be used to relate non-training inputs to new outputs in a way that (given a sufficient training set) follows input-output correlations found in the training examples.

In some embodiments, an anatomical schema 204A is built at least partially on the basis of machine learning results. In some embodiments, preparation of the training examples is performed on the basis of an anatomical schema framework which already includes many of the general features of the anatomical schema (e.g., which anatomical features are adjoining to and/or contained by other features), but also has placeholder and/or empty functions for at least some of the functions that relate recorded measurement data to anatomical identities and/or recommended procedure actions. Machine learning results are optionally used to supply practical versions of these functions.

Measurement data 206 (described, for example, in relation to FIG. 1A) is largely what comprises the "input" side of the training examples, though the training example input may also be considered to include such things as patient history and other patient data, imaging data obtained outside of the procedure itself, and/or procedure design and parameters. As previously noted, in intervention procedures performed over catheter by indirect visualization, nearly all of the inputs and many outputs generated during a procedure are available in the same digital form originally available to practitioner.

Supervisory signals 363, in some embodiments, comprise at least one of:

operator's anatomical identifications 354 (optionally, these are provided by the operator in real time or corrected by the operator post-procedure. Correction may be applied to operator's provided identification and/or to outputs of a previously available anatomical schema);

operator's actions 356 (what the operator actually did in a certain input context may be considered as an output reflecting the particular expertise of the operator);

operator's other annotations 358 (for example, indications by an operator as to which particular parts of measurement data 206 were most relevant to anatomical identifications and/or actions);

post-processing annotations 360 (e.g., corrections of errors, linkage of outputs and inputs which are separated in the raw data such as ablation validations, annotations to interpret data and/or actions in terms defined by the anatomical schema framework 350); and/or procedure outcomes 362 (e.g., results of a procedure which may only become known after the procedure itself is complete).

At block 366, in some embodiments, the training examples are optionally further processed so that appropriate epochs of a procedure are assigned to be associated with the correct schema entries of the anatomical schema framework 350 (e.g., annotated so that they are associated with their correct anatomical and/or procedural context). The result of this, and any optional further post-processing such as normalization, is provided as post-processed training examples 352.

At block 368, the machine learning itself is performed, based on the post-processed training examples 352. Optionally, any suitable machine learning technique is used, for example, artificial neural network, back propagation, Bayesian statistics, case-based reasoning, decision tree learning, inductive logic programming, Gaussian process regression, group method of data handling, kernel estimators, learning classifier systems, multilinear subspace learning, naive Bayes classifier, maximum entropy classifier, conditional random field, nearest neighbor algorithm, probably approximately correct learning, symbolic machine learning algorithms, subsymbolic machine learning algorithms, support vector machines, minimum complexity machines, random forests, ensembles of classifiers, ordinal classification, data pre-processing, statistical relational learning, and/or another machine learning technique.

At block 370, in some embodiments, the results of the machine learning at block 368 are assigned to the anatomical schema framework to produce an updated anatomical schema 204A.

Figure 4A:
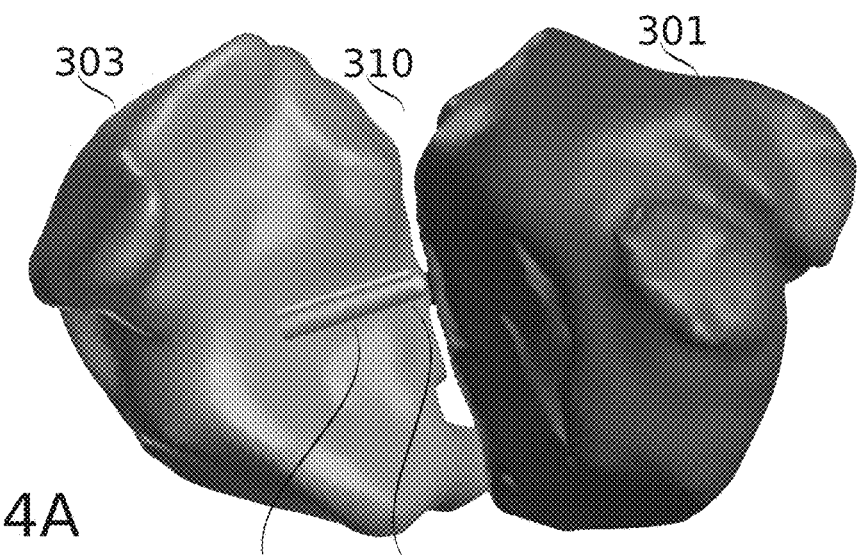
FIGS. 4A-4C schematically represent crossing by a catheter probe from a right atrium across an interatrial septum to a left atrium via a fossa ovalis, according to some embodiments of the present disclosure.
Figure 4B:
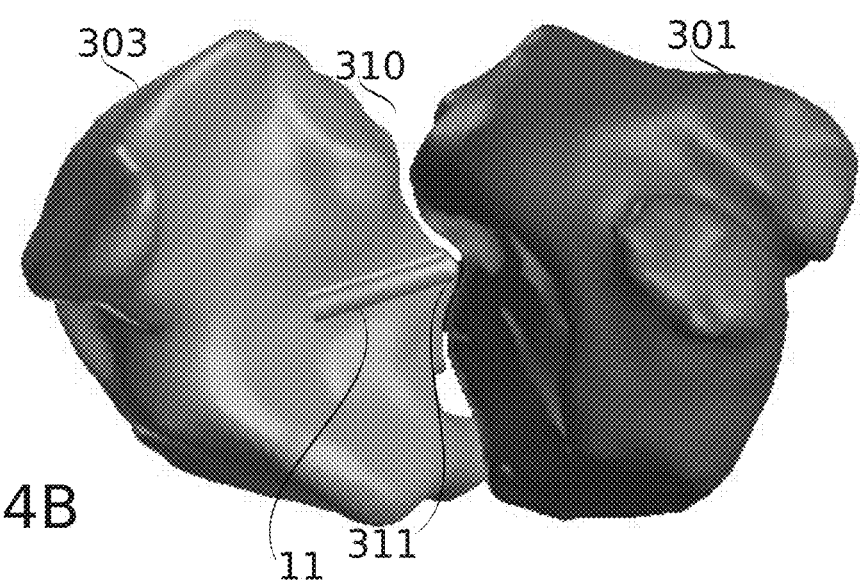
Figure 4C:
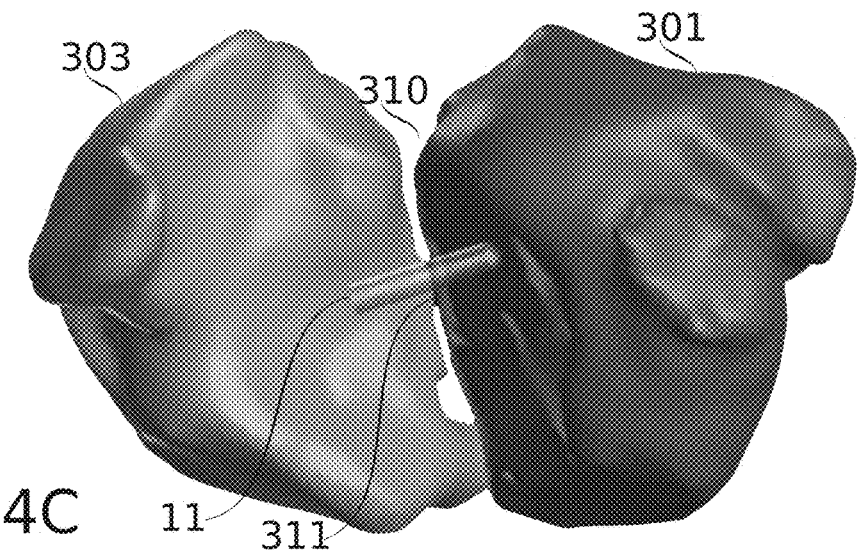

Examples of Procedure Operations Used with Automatic Target/Action Selection Interatrial Septum Crossing Reference is now made to FIGS. 4A-4C, which schematically represent crossing by a catheter probe 11 from a right atrium 303 across an interatrial septum 310 to a left atrium 301 via a fossa ovalis 311, according to some embodiments of the present disclosure.

In FIG. 4A, probe 11 has found fossa ovalis 311, and is positioned against it. In FIG. 4B, probe 11 is pressing against fossa ovalis 311, causing "tenting" of the interatrial septum 310. In FIG. 4C, probe 11 has penetrated the fossa ovalis, releasing the tenting, and leaving probe 11 temporarily embedded half-way through the interatrial septum 310.

Different methods may be used to help encourage the crossing of a probe 11 at a crossing location as shown. Descriptions in relation to FIG. 11, herein, describe how ablation by a probe (e.g., RF ablation) may be used to assist crossing, potentially allowing a "single catheter" procedure for ablation to treat atrial fibrillation. Descriptions in relation to FIG. 6, herein, describe electrically monitored use of a needle to cross the interatrial septum.

Reference is now made to FIG. 5, which is a schematic flowchart describing a method of locating a fossa ovalis, according to some embodiments of the present disclosure.

At block 510, in some embodiments, a catheter probe 11 is navigated into contact with the interatrial septum (IAS). Discovery of the position of the IAS, for example with respect to the orientation of the IVC and SVC (optionally with assistance from the identification of the Eustachian valve) is provided in descriptions of FIG. 3A, in relation to an example of a schema entry for an interatrial septum 310. It is noted in particular that in some embodiments, a full right atrium map is optionally not generated—it is potentially sufficient to find the IAS, and scan it (by probe movements) in the general region where the fossa ovalis is expected to lie.

At block 512, in some embodiments, the catheter probe 11 is moved over the IAS while making dielectric measurements. It is generally not necessary to completely dielectrically map the IAS.

At block 514, in some embodiments, the foramen ovalis or patent foramen ovale (PFO) (according to which is present) is identified.

In some embodiments, a fossa is identified based on a combination of voltage and/or impedance signals measured from probe electrodes 3, and geometrical considerations. The fossa is characteristically the thinnest zone in the septum (although in rare occasions it is lipomatous and thickened). A typical dielectric signature will vary from surrounding wall over a characteristics diameter of about 5-10 mm. Geometrically, the fossa is located about halfway between the SVC and IVC on the septal wall, between the septum primum and the septum secundum. The anatomical variant of an adult PFO may additionally or alternatively be identified as an open transseptal tract because the catheter probe simply crosses into the left atrium when it is pressed against the region of the PFO. It is noted that initially small 3-4 mm PFOs potentially increase in diameter with aging and can become stretched up to 7-10 mm (resembling a small to moderate atrial septal defect).

Monitored Needle Interatrial Septum Crossing

Figure 6:
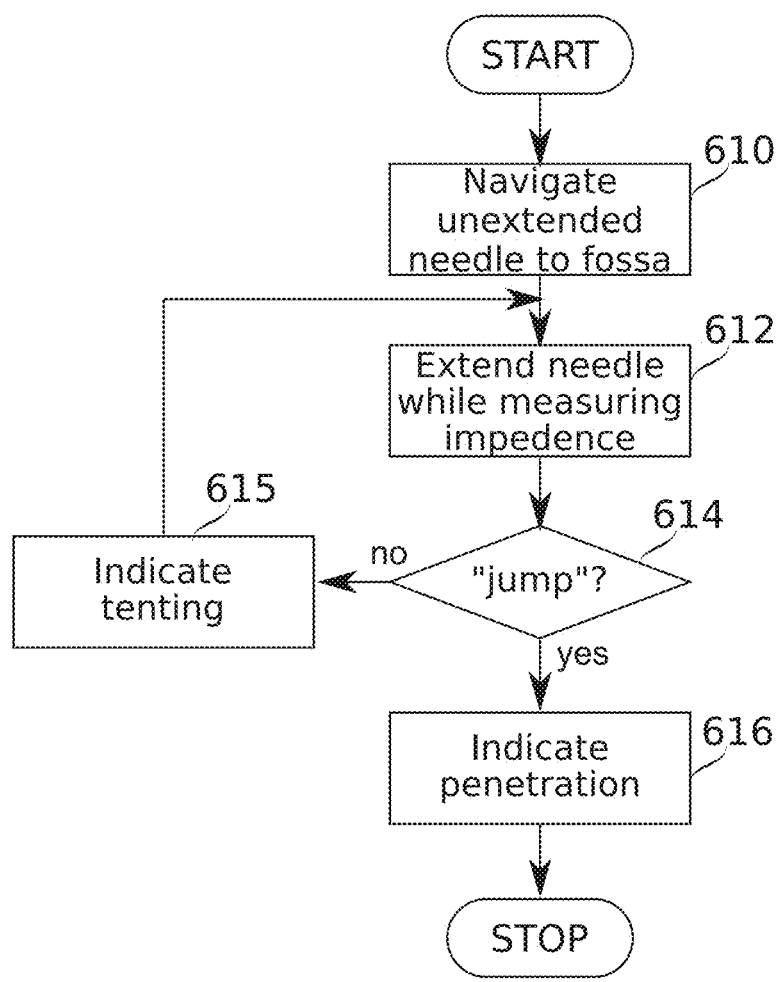
FIG. 6 is a schematic flowchart describing a method of crossing a fossa ovalis using an electrically monitored needle, according to some embodiments of the present disclosure.

Reference is now made to FIG. 6, which is a schematic flowchart describing a method of crossing a fossa ovalis using an electrically monitored needle, according to some embodiments of the present disclosure.

Electrical monitoring of interatrial septum crossing using a Brackenrough needle and a NavX system (EnSite) has been described based on spatial position monitoring (Sumit Verma and Mark Borganelli, *Real-Time, Three-Dimensional Localization of a Brockenbrough Needle during Transseptal Catheterization Using a Nonfluoroscopic Mapping System*, J. Invasive Card., 18:7 (2006)). In some embodiments of the present disclosure, features of the electrical changes which occur during this penetration (not necessarily observations of position per se) are used to generate a visual representation of the procedure which evokes the "tenting" phenomenon which may be observed, e.g., under direct imaging visualization of a transseptal penetration.

The flowchart begins, and at block 610, in some embodiments, a catheter including a transseptal needle encased in a sheath is navigated to the region of a fossa ovalis. The needle itself (which is quite long, e.g., about 70-110 cm long, so that it may extend out of the body even with its tip inside the heart) can be used as a sensing electrode by electrically connecting it to, e.g., electrical field generator/measurer 10. Optionally, a proximal part of the needle is connected using an alligator clip through the pin-box to the system, converting it to a long, though insulated along its length, unipolar electrode.

In some embodiments, the transseptal needle itself is used to find the fossa ovalis, for example, as described in relation to FIG. 5. Optionally, the fossa ovalis is found separately from the action of crossing the fossa ovalis using the needle.

At block 612, in some embodiments, the needle is gradually extended from its sheath. The progress of the operation is optionally tracked by noting the changes in electrical signal as more and more of the needle is protruded from the electrically insulating sheath.

At block 614, in some embodiments, detection is made as to whether or not a sudden jump in electrical signal amplitude has occurred.

If not, optionally (at block 615), a display (e.g. on user interface 40) presents penetration progress to an operator by imitating the typical 'tenting' of the IAS before a successful puncture. Flow continues with a return to block 612.

Otherwise, at block 616, the jump is interpreted as a successful penetration. The "tenting" display is optionally returned to the IAS's resting position, but with the penetration needle now shown crossing the IAS. The flowchart ends.

Monitored Cryoballoon Ablation

Figure 7A:
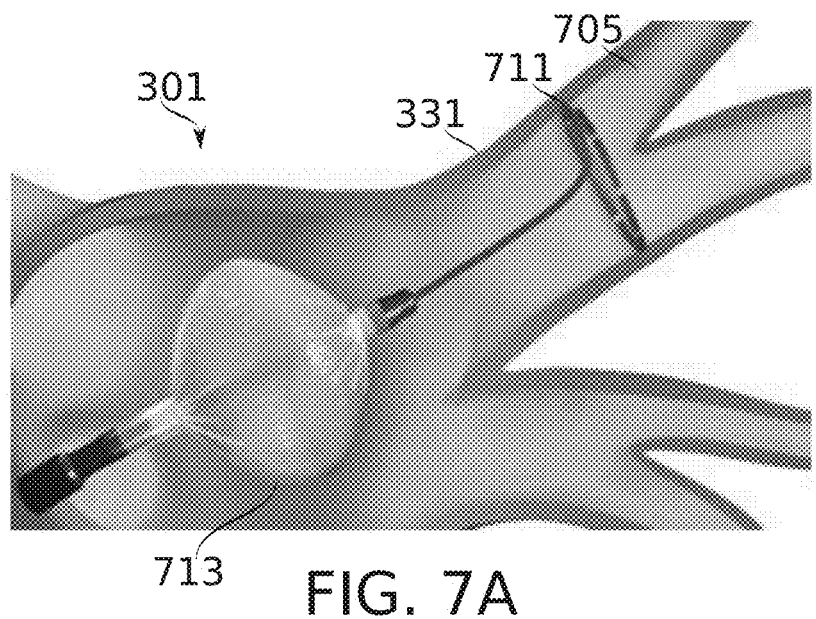
FIGS. 7A-7B schematically represent stages in cryoablation including insertion of a lasso catheter probe into a pulmonary vein of a left atrium, and conversion of blood flow into blocked flow as a cryoballoon is pressed firmly up against the ostium leading into pulmonary vein, according to some embodiments of the present disclosure.
Figure 7B:
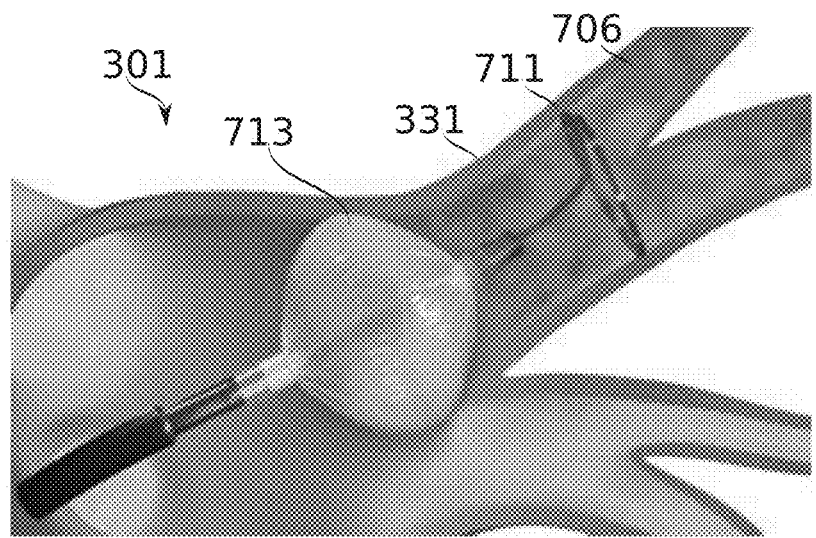
Figure 8:
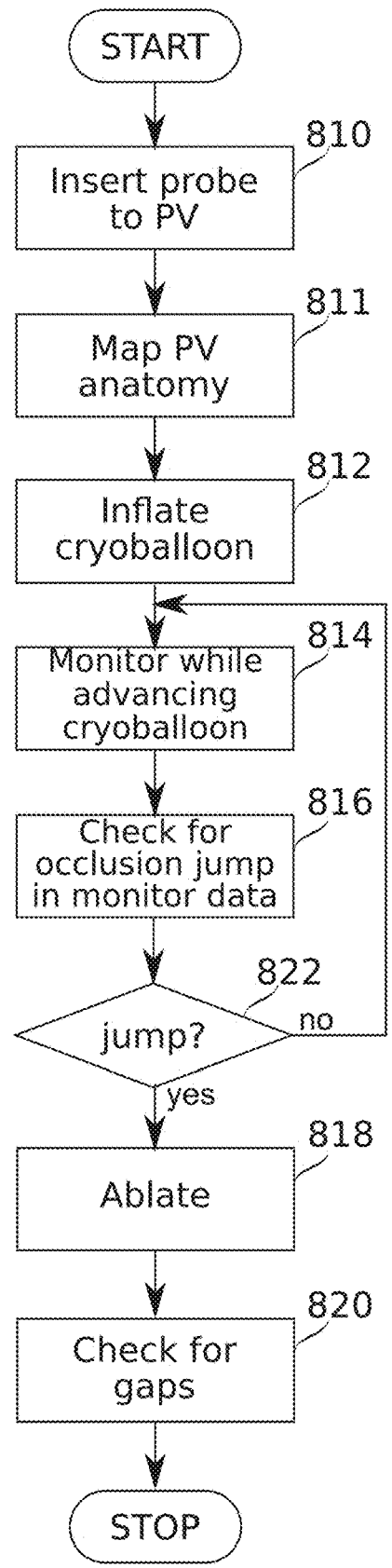
FIG. 8 is a schematic flowchart describing a method for electrical monitoring of the flow blockage shown in FIGS. 7A-7B, according to some embodiments of the present disclosure.

Reference is now made to FIGS. 7A-7B, which schematically represent stages in cryoablation including insertion of a lasso catheter probe 711 into a pulmonary vein 331 of a left atrium 301, and conversion of blood flow 705 into blocked flow 706 as a cryoballoon 713 is pressed firmly up against the ostium leading into pulmonary vein 331, according to some embodiments of the present disclosure. Reference is also made to FIG. 8, which is a schematic flowchart describing a method for electrical monitoring of the flow blockage 706 shown in FIGS. 7A-7B, according to some embodiments of the present disclosure.

At block 810, in some embodiments, the looped (lasso) region of a catheter probe configured like the lasso-and-balloon probe 711 of FIG. 7A is inserted to a pulmonary vein (PV). At block 811, the PV anatomy is mapped, for example to verify that the geometry is of an appropriate size and shape to allow use of the cryoballoon 713 to make a complete ablation around the ostium of the PV. In some embodiments, mapping the PV anatomy may include moving one or more electrodes of probe 711 while tracking its position, and determining the limits of its movement and/or positions at which the electrodes experience a change in measured impedance indicative of contact with and/or proximity to a cavity wall.

At block 812, in some embodiments, the cryoballoon is optionally inflated, and the catheter probe 711 positioned in a state like that shown in FIG. 7A—balloon inflated, but not yet positioned to press against the PV ostium. Alternatively, in some embodiments, the balloon is advanced into position while remaining deflated, and is gradually inflated in place.

At block 814, the cryoballoon is advanced towards (and/or inflated within) the PV ostium while electrically monitoring voltages generate from electrodes of the lasso catheter probe 711 using those same electrodes. During advancing/inflating, at block 816, a check is made for an occlusion jump in the monitoring data (that is, a relatively sudden change in voltage). Such a jump (for example, a jump of at least 3 times the high-frequency noise amplitude occurring, for example, within 100 msec, 200 msec, 500 msec, 1 seconds, or 2 seconds) has been observed by the inventors in association with the completion of sealing of the PV ostium by the advancing cryoballoon. In some embodiments, one or more characteristics of a change in voltage which is recognized in the check as comprising such a jump are predetermined. For example, the characteristics are optionally defined according to their time course, frequency, and/or amplitude. Optionally, the characteristics are predetermined by use of a machine learning result, e.g., a weighting data structure created from training examples associated with feedback categorizing them as "jump" or "non-jump".

At block 822, if the jump has not yet been noted, the flowchart returns to block 814. Otherwise, the flowchart continues at block 818 with cryoablation (e.g., filling of the cryoballoon with cryogenic fluid to induce a preferably circular lesion around a periphery of the PV ostium). Optionally, after the completion of ablation, electrodes of the lasso probe (or another probe) are used (at block 820) to check the resulting lesion for gaps, for example using impedance measurements. An example of data resulting from such a check in a phantom pig heart is provided in FIGS. 10A-10B. Optionally (not shown) gaps are repaired by additional cryoballoon lesioning and/or targeted RF lesioning.

A potential advantage of the method of FIG. 8 for monitoring occlusion is to avoid a need for X-ray imaging and/or contrast medium injection to verify that a good balloon-tissue contact has been accomplished.

Reference is now made to FIGS. 9A-9D, which schematically represent test results of the method of FIG. 8, according to some embodiments of the present disclosure.

Figure 9A:
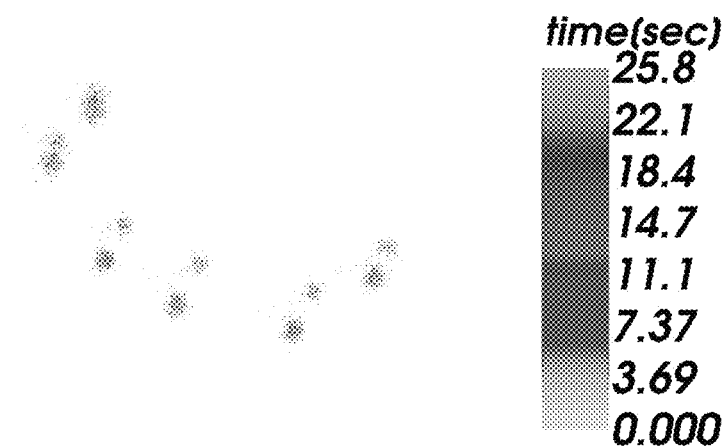
FIGS. 9A-9D schematically represent test results of the method of FIG. 8, according to some embodiments of the present disclosure.

FIG. 9A shows changes in sensed voltage at two particular frequencies (of an optional multiplicity of frequencies which may be used), from a plurality of electrodes such as the lasso electrodes of catheter probe 711. Results from six electrodes are shown. It may be observed that there appears to be a relatively sudden jump at around 18 seconds from a cluster of early voltage values to a cluster of later-recorded voltage values. These jumps correlate with the moment of sealing contact between the cryoballoon (a Medtronic Arctic Front cryoballoon) and a water-immersed pig heart phantom, as indicated by reduction of fluid flow maintained by a syringe attached to an open tube through the phantom PV to zero.

Figure 9B:
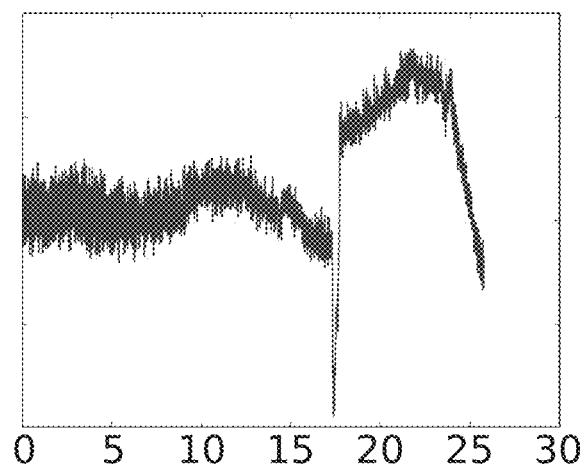
Figure 9C:
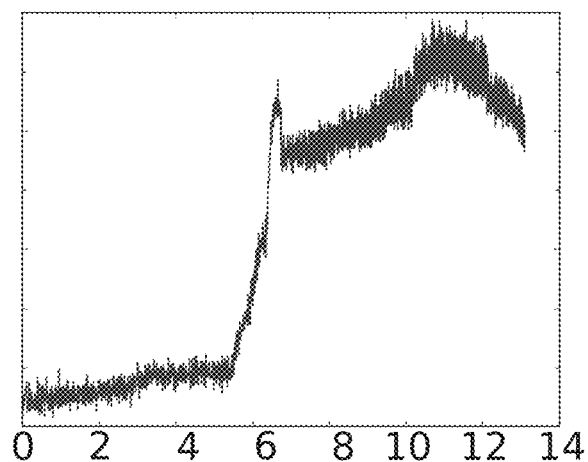

FIGS. 9B-9C show onset and offset of the voltage jump for a single electrode, including a voltage jump in FIG. 9B when flow was stopped by the cryoballoon (at about 18 seconds), and other jump at about 7 seconds in FIG. 9C when flow was resumed (by deflation/moving of the cryoballoon).

Figure 9D:
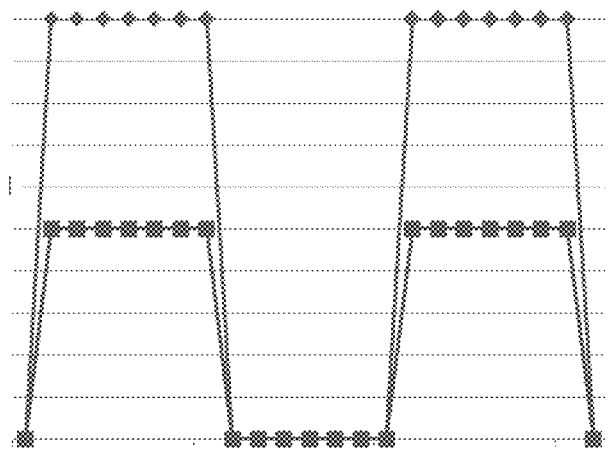

FIG. 9D shows second-by-second correlations between measured flow velocity (square data points) and the voltage jump signal (diamond data points), strengthening the case for a causal association between balloon sealing and the voltage jump.

Figure 10A:
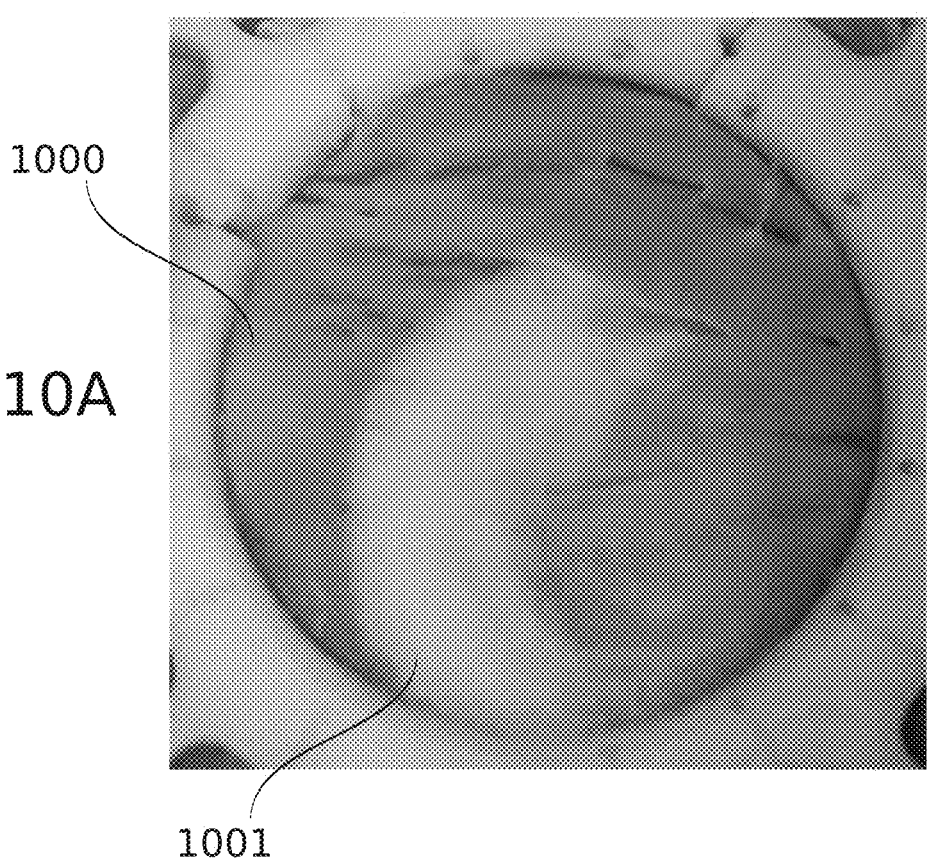
FIGS. 10A-10B respectively represent visual results of cryoablation in vitro on a muscle tissue preparation (FIG. 10A), and dielectric assessment of the same results (FIG. 10B) which reveals a potential gap in the apparently well-ablated region, according to some embodiments of the present disclosure.
Figure 10B:
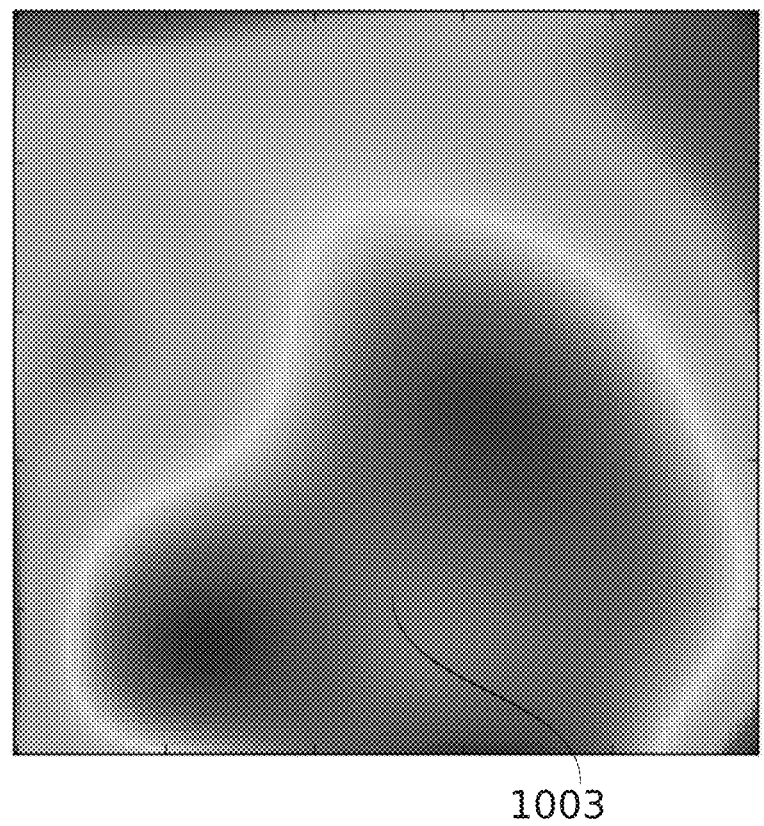

Reference is now made to FIGS. 10A-10B, which respectively represent visual results of cryoablation in vitro on a muscle tissue preparation 1000 (FIG. 10A), and dielectric assessment of the same results (FIG. 10B) which reveals a potential gap 1003 in the apparently well-ablated region 1001.

Another potential advantage of the method of FIG. 8 is that the electrodes of the lasso are nearly in position to be repositioned to measure the possible presence of ablation gaps, so that remedial action can be taken immediately, potentially before the full onset of tissue reactions such as edema which can interfere with the effectiveness of subsequent ablation attempts.

The light-colored region 1001 of FIG. 10A is discolored due to previous exposure to cryoablation (the lesion is not circular because of the flat geometry of the test preparation). However, upon dielectric measurement of tissue properties in the area, it was found that a partial gap indicated in region 1003 remained. Dielectric measurement of tissue lesion properties is described, for example, in International Patent Publication No. WO2016/181318, entitled LESION ASSESSMENT BY DIELECTRIC PROPERTY ANALYSIS, and published on Nov. 17, 2016.

Single Catheter Transseptal Access and Left Atrium Ablation

Figure 11:
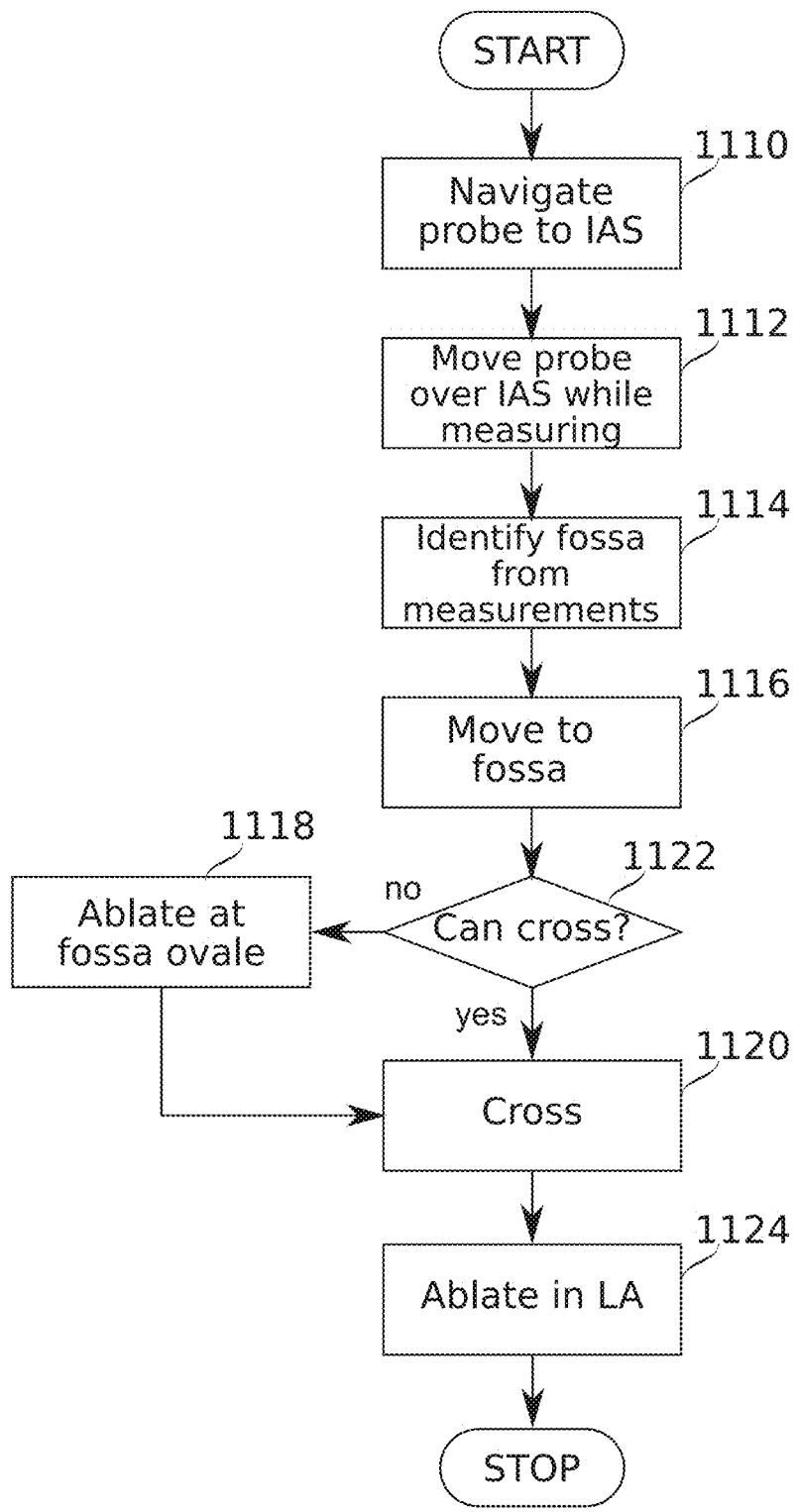
FIG. 11 is a schematic flowchart describing a method for single-electrode transseptal penetration from the right to the left atria, followed by ablation within the left atrium, according to some embodiments of the present disclosure.

Reference is now made to FIG. 11, which is a schematic flowchart describing a method for single-electrode transseptal penetration from the right to the left atria, followed by ablation within the left atrium, according to some embodiments of the present disclosure.

Blocks 1110-1114, in some embodiments, correspond to blocks 510, 512, and 514 of FIG. 5.

At block 1110, in some embodiments, a catheter probe 11 comprising at least a tip electrode configured to act as an RF ablation probe is navigated to an IAS by any suitable method, for example as described in relation to FIG. 3A, herein. At block 1112, the probe is moved over the IAS while making dielectric measurements, and at block 1114, the fossa ovalis (or patent foramen ovale, according to the anatomy) is identified from the dielectric measurements. At block 1116, the probe is moved to the fossa/PFO (if it is not there already). At block 1122, a determination is made as to whether the ablation catheter probe 11 can already cross the septum (e.g., because there is a PFO). If not, then at block 1118, the RF ablation electrode of the catheter is activated to ablate at the fossa ovale. Optionally, ablation settings used are similar to those used in normal transmural ablation for AF treatment. Optionally, the ablation settings are more aggressive, however, in order to achieve substantial mechanical weakening of the IAS structure which is normally preferably avoided in AF lesion treatments. Potentially, the ablation weakens the already thin fossa ovalis sufficiently to allow the catheter probe 11 to penetrate it through the use of blunt force. From which ever branch of the method, at block 1120, in some embodiments, the catheter probe is pushed across the IAS. The catheter is navigated into position to perform ablation treatments, and at block 1124, in some embodiments, ablation in the left atrium (e.g., ablation to encircle PVs with ablation lines) is performed.

Potentially, crossing the IAS without a transseptal needle is advantageous economically, e.g., for requiring fewer tools and/or fewer tool changes during a procedure. Crossing by applying RF energy is optionally performed, for example, with a dedicated Baylis system and/or a standard RF generator.

It is expected that during the life of a patent maturing from this application many relevant position tracking methods will be developed; the scope of the term "position tracking" is intended to include all such new technologies a priori.

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of determining, during a medical procedure, an anatomical identity of a first intrabody region which is a region included in a second intrabody region, the first and second intrabody regions being, in a body of a patient undergoing the medical procedure, the procedure using an intrabody probe, the method characterizing a position of the intrabody probe, and the method comprising:
   receiving data indicating that the intrabody probe is operating in an operational context, a specification of the operational context including a condition indicative of proximity of the intrabody probe to the second intrabody region;
   receiving input data from the intrabody probe indicating one or more measured properties of the first intrabody region;

wherein the input data is received while the intrabody probe moves, and the condition indicative of proximity remains satisfied;

selecting at least one rule for anatomical identification from an anatomical schema, wherein the at least one rule is selected, based on the operational context, from a set of a plurality of different rules, wherein one or more of said different rules is associated with one or more operational contexts different from and exclusive to said operational context; and applying the at least one rule to the input data, to determine anatomical identity of the first intrabody region, also while the condition indicative of proximity remains satisfied, thereby characterizing the position of the intrabody probe with respect to the first intrabody region included in the second intrabody region.

2. The method of claim 1, comprising associating the anatomical identity determined for the first intrabody region to a geometrical representation of the first intrabody region within the second intrabody region.

3. The method of claim 2, comprising displaying the anatomical identity determined for the first intrabody region together with a display of the geometrical representation of the first intrabody region within the second intrabody region.

4. The method of claim 1, comprising guiding navigation of the intrabody probe to the first intrabody region, based on the anatomical identity determined for the first intrabody region and the characterization of the position of the intrabody probe with respect to the first and second intrabody regions.

5. The method of claim 1, comprising using the intrabody probe to perform an action upon the first intrabody region, based on the anatomical identity determined for the first intrabody region.

6. The method of claim 1, wherein the input data does not include image data.

7. The method of claim 6, wherein the data indicating a current operational context comprise non-image data.

8. The method of claim 1, wherein the input data comprises electrical measurements from the intrabody region.

9. The method of claim 8, wherein the electrical measurements comprise voltage measurements.

10. The method of claim 8, wherein the electrical measurements comprise impedance measurements.

11. The method of claim 1, wherein the operational context comprises an anatomical location of the intrabody probe.

12. The method of claim 1, wherein the operational context comprises the nature of the medical procedure.

13. The method of claim 1, wherein at least two of the different rules in the set of rules are different in one or more parameter value of a same parameter.

14. The method of claim 1, wherein selecting at least one rule based on the operational context comprises selecting a rule for identifying a particular target tissue based on the operational context.

15. The method of claim 1, wherein selecting at least one rule based on the operational context comprises selecting a rule which takes into account changes in measurement data based on the operational context.

16. The method of claim 1, wherein said operational context has a first identification rule or a first action rule associated to be applied therewith, when said operational context is indicated; and wherein said plurality of operational contexts includes a plurality of additional operational contexts, in addition to said operational context, each said additional operational context of said plurality of additional operational contexts corresponding to a different phase of said medical procedure, each of said additional operational contexts having associated to be applied therewith at least one identification rule not associated to be applied with said operational context when indicated, or an action rule not associated to be applied with said operational context when indicated.

17. A method of determining, during a medical procedure, an anatomical identity of a first intrabody region comprising a fossa ovalis and included in a second intrabody region comprising an interatrial septum, the first and second intrabody regions being in a body of a patient undergoing the medical procedure, the procedure using an intrabody probe, the method characterizing a position of the intrabody probe, and the method comprising:

receiving data indicating that the intrabody probe is operating in an operational context, a specification of the operational context including a condition indicative of proximity of the intrabody probe to the second intrabody region;

receiving input data from the intrabody probe indicating one or more measured properties of the first intrabody region;

wherein the input data is received while the intrabody probe moves, and the condition indicative of proximity remains satisfied;

selecting at least one rule for anatomical identification from an anatomical schema, wherein the at least one rule is selected, based on the operational context, from a set of a plurality of different rules, wherein one or more of said different rules is associated with one or more operational contexts different from and exclusive to said operational context; and applying the at least one rule to the input data, to determine anatomical identity of the first intrabody region, also while the condition indicative of proximity remains satisfied, thereby characterizing the position of the intrabody probe with respect to the fossa ovalis of the first intrabody region included in the interatrial septum of the second intrabody region.

* * * * *